United States Patent
Bermeister et al.

(10) Patent No.: US 10,854,314 B2
(45) Date of Patent: Dec. 1, 2020

(54) SYSTEMS, METHODS, AND DEVICES FOR ANALYSIS OF GENETIC MATERIAL

(71) Applicant: CODONDEX LLC, Sherman Oaks, CA (US)

(72) Inventors: Kevin Bermeister, Sherman Oaks, CA (US); Xinghao Yu, Ashfield (AU)

(73) Assignee: CODONDEX LLC, Sherman Oaks, CA (US)

( * ) Notice: Subject to any disclaimer, the term of this patent is extended or adjusted under 35 U.S.C. 154(b) by 260 days.

(21) Appl. No.: 15/345,505

(22) Filed: Nov. 7, 2016

(65) Prior Publication Data

US 2017/0270240 A1 Sep. 21, 2017

Related U.S. Application Data

(63) Continuation of application No. PCT/US2015/030478, filed on May 13, 2015.
(Continued)

(51) Int. Cl.
*G01N 33/48* (2006.01)
*G01N 33/50* (2006.01)
(Continued)

(52) U.S. Cl.
CPC ............ *G16B 20/00* (2019.02); *G16B 30/00* (2019.02); *G16B 40/00* (2019.02); *G16B 50/00* (2019.02)

(58) Field of Classification Search
None
See application file for complete search history.

(56) References Cited

U.S. PATENT DOCUMENTS 8,725,422 B2 5/2014 Halpern et al.
10,679,727 B2 6/2020 Ding et al.
(Continued)

FOREIGN PATENT DOCUMENTS

CN 102762743 A 10/2012
CN 103201744 A 7/2013
(Continued)

OTHER PUBLICATIONS

Levinson et al. Slipped-strand mispairing: A major mechanism for DNA sequence evolution. Molecular Biology and Evolution, vol. 4, pp. 203-221. (Year: 1987).*
(Continued)

*Primary Examiner* — Russell S Negin
(74) *Attorney, Agent, or Firm* — Siritzky Law, PLLC; Brian Siritzky

(57) ABSTRACT

A representation of a nucleic acid sequence encodes a particular gene having at least one intron. An intron signature value corresponding to the at least one intron is determined based on a first computational function applied to at least one portion of the representation of the nucleic acid sequence corresponding to the at least one intron. A protein signature value is determined, being based on a second computational function applied to a representation of a protein. In a database, an association is formed between the intron and protein signature values. This process is repeated for each of a plurality of nucleic acid sequences. Nucleic acid sequences in the database are ordered based on a sort of corresponding intron signature values. An ordering determined by the sort is used to determine or confirm a role or function of a portion of a given nucleic acid sequence.

28 Claims, 25 Drawing Sheets

Specification includes a Sequence Listing.

Related U.S. Application Data

(60) Provisional application No. 61/993,846, filed on May 15, 2014, provisional application No. 62/015,492, filed on Jun. 22, 2014.

(51) Int. Cl.
  *G16B 20/00* (2019.01)
  *G16B 30/00* (2019.01)
  *G16B 40/00* (2019.01)
  *G16B 50/00* (2019.01)

(56) References Cited

U.S. PATENT DOCUMENTS

| | | |
|---|---|---|
| 2009/0208955 A1 | 8/2009 | Harlan et al. |
| 2011/0144914 A1 | 6/2011 | Harrington et al. |
| 2016/0188797 A1 | 6/2016 | Chang et al. |

FOREIGN PATENT DOCUMENTS

| | | |
|---|---|---|
| CN | 104699998 A | 6/2015 |
| WO | 2015081754 A1 | 3/2015 |
| WO | 2015175602 A1 | 11/2015 |

OTHER PUBLICATIONS

Gotoh, Osamu. Homology-based gene structure prediction: simplified matching algorithm using a translated codon (tron) and improved accuracy by allowing for long gaps. Bioinformatics, 2000, 16.3: 190-202.

Nagasaki, Hideki, et al. Automated classification of alternative splicing and transcriptional initiation and construction of visual database of classified patterns. Bioinformatics, 2006, 22.10: 1211-1216.

Gopalan, Vivek, et al. Xpro: database of eukaryotic protein-encoding genes. Nucleic acids research, 2004, 32.suppl I: D59-D63.

International Preliminary Report on Patentability Chapter I, for PCT/US2015/030478, WIPO, Nov. 15, 2016.

International Search Report, for PCT/US2015/030478, WIPO, dated Sep. 8, 2015.

Written Opinion of the International Searching Authority, for PCT/US2015/030478, WIPO, dated Sep. 8, 2015.

International Search Report, for PCT/IB2018/050053, WIPO, dated Feb. 12, 2018.

Written Opinion of the International Searching Authority, for PCT/IB2018/050053, WIPO, dated Feb. 12, 2018.

WIPO, International Preliminary Report on Patentability Chapter I received in International Application No. PCT/IB2018/050053, Feb. 2, 2018, (9p.).

Yipeng, "Softman Subject Analysis and Information Retrieval Technique", English Translation Beijing University of Posts and Telecommuncations Press, Aug. 2012, pp. 149-156.

Chinese Office Action received in Chinese Application No. 201880012087.0, dated Apr. 15, 2020, (12p.).

Search Report received in Chinese Application No. 201880012087.0, dated Apr. 15, 2020, (2p.).

"Command and Control Information Precision Service", Chen Honghui National Defense Industry Press, published Jul. 31, 2015, pp. 186-191 (cited as "A" reference in Search Report received in Chinese Application No. 201880012087.0, dated Apr. 15, 2020.

* cited by examiner

| Signature | DNA Sequence ID. | Intron Seq. IDs. | Exon Seq. IDs. | Genetic Function(s) | Protein ID. |
|---|---|---|---|---|---|
| S0 | $ID_0$ | ID-I-0 ... | ID-E-0 ... | F0 ... | P0 |
| ⋮ | | | | | |
| SK | IDK | ID-I-K ... | IE-E-K ... | PK | |
| ⋮ | | | | | |
| SN | $IN_N$ | ID-I-N ... | ID-E-N ... | PN | |

FIG. 2-A

| Sequence ID. | Sequence |
|---|---|
| S0 | Sequence #0 |
| ⋮ | ⋮ |
| SJ | Sequence #J |

| TRANSCRIPT | INTRON | FORWARD INTRON-PROTEIN PROTEIN SORT | FORWARD INTRON-PROTEIN PRO MIN | FORWARD INTRON-PROTEIN INTRON PROTE | REVERSE INTRON-PROTEIN INTR PRO MIN | REVERSE INTRON-PROTEIN INTRON SORT | PROTEIN SORT | FORWARD+REVERSE INTRON-PROTEIN INTRON | PROTEIN |
|---|---|---|---|---|---|---|---|---|---|
| ENST00000413626 | 13 | 15 | ## | 6 | 9 | ## | 1 | 887952281200868857 | 1729869657710485483 |
| ENST00000377326 | 1 | 12 | # | 2 | 12 | ## | 2 | 1310430311095040203 | 9615823206228663331 |
| ENST00000429702 | 6 | 11 | # | 9 | 14 | ## | 3 | 2063183349407904355 | 2263954643625590701 |
| ENST00000424912 | 3 | 10 | # | 15 | 15 | ## | 4 | 4576144991289260531 | 2263954643625590701 |
| ENST00000394376 | 10 | 7 | # | 11 | 5 | ## | 5 | 6708259094357667407 | 1685576919241470079 |
| ENST00000377321 | 7 | 9 | # | 4 | 8 | ## | 6 | 8075656226753920645 | 4628150512775047415 |
| ENST00000377316 | 14 | 1 | # | 13 | 1 | ## | 7 | 8785326746195670043 | 1175752382456687954 |
| ENST00000443283 | 15 | 8 | ## | 10 | 4 | ## | 8 | 10564216813085021255 | 1685576919241470079 |
| ENST00000394374 | 4 | 4 | # | 5 | 2 | ## | 9 | 11333147157648448431 | 1685576919241470079 |
| ENST00000450708 | 11 | 2 | # | 3 | 7 | ## | 10 | 12454458814781236391 | 8956001353592653527 |
| ENST00000440873 | 12 | 3 | # | 7 | 10 | ## | 11 | 13201712806137462353 | 3477712031604516857 |
| ENST00000377313 | 5 | 5 | # | 14 | 6 | ## | 12 | 14242566224793934807 | 1685576919241470079 |
| ENST00000557652 | 9 | 6 | # | 8 | 3 | ## | 13 | 16399785077146281741 | 1685576919241470079 |
| ENST00000315422 | 2 | 13 | # | 12 | 13 | ## | 14 | 17088450819809387979 | 9615823206228663331 |
| ENST00000312049 | 8 | 14 | # | 1 | 9 | ## | 15 | 17187019405732497315 | 9615823206228663331 |

| Cotrotex | GENES | HASH ALGORITHM | HASH PATTERN | GENE INFO LIST |
|---|---|---|---|---|

| NAME | SPECIES | SOURCE | SOURCE LINK |
|---|---|---|---|
| MEN1 | HOMO SAPIENS | ENSEMBL | HTTP://ASIA.ENSEMBL.ORG/HOMO_SAPIENS/GENE/SUMMARY?G=ENSG00000133895 |
| ST5 | HOMO SAPIENS | ENSEMBL | HTTP://ASIA.ENSEMBL.ORG/HOMO_SAPIENS/GENE/SUMMARY?G=ENSG00000166444 |
| IRF3 | HOMO SAPIENS | ENSEMBL | HTTP://ASIA.ENSEMBL.ORG/HOMO_SAPIENS/GENE/SUMMARY?G=ENSG00000126456 |
| ZNF692 | HOMO SAPIENS | ENSEMBL | HTTP://ASIA.ENSEMBL.ORG/HOMO_SAPIENS/GENE/SUMMARY?G=ENSG00000171163 |

*FIG. 6-A*

| Cobrrix | GENES | HASH ALGORITHM | HASH PATTERN | GENE INFO LIST |

| GENE: MEN1 |
| SUMMARY |
| TRANSCRIPTS |

NAME: MEN1
LOCATION: CHROMOSOME 11:64570988-64578766:-1
BIOTYPE: PROTEIN_CODING
SPECIES: HOMO_SAPIENS
DESCRIPTION: MULTIPLE ENDOCRINE NEOPLASIA I[SOURCE:HGNC SYMBOL ACC:7010]
SEQUENCE NAME: CHROMOSOME:GRCh37:11:1:135006516:1
SEQUENCE START: 64570988
SEQUENCE END: 64578766
SEQUENCE STRAND: -1
SEQUENCE LENGTH: 135006516
SOURCE: HTTP://ASIA.ENSEMBL.ORG/HOMO_SAPIENS/GENE/SUMMARY?G=ENSG00000133895

*FIG. 6-B*

| Codrntx | GENES | HASH ALGORITHM | HASH PATTERN | GENE INFO LIST |
|---|---|---|---|---|

GENE: MEN1
SUMMARY
TRANSCRIPTS

TRANSCRIPTS

| TRANSCRIPT ID | SEQUENCE NAME | ACTION |
|---|---|---|
| ENST00000377316 | 11:64570988:64577957:-1 | MORE DETAILS |
| ENST00000377321 | 11:64570988:64578030:-1 | MORE DETAILS |
| ENST00000377326 | 11:64570988:64578080:-1 | MORE DETAILS |
| ENST00000312049 | 11:64570988:64578188:-1 | MORE DETAILS |
| ENST00000315422 | 11:64570988:64578213:-1 | MORE DETAILS |
| ENST00000377313 | 11:64571806:64577604:-1 | MORE DETAILS |
| ENST00000440873 | 11:64573714:64578030:-1 | MORE DETAILS |
| ENST00000450708 | 11:64574552:64578053:-1 | MORE DETAILS |
| ENST00000413626 | 11:64575024:64577993:-1 | MORE DETAILS |
| ENST00000429702 | 11:64577142:64578766:-1 | MORE DETAILS |
| ENST00000424912 | 11:64577142:64578766:-1 | MORE DETAILS |
| ENST00000337652 | 11:64570996:64578766:-1 | MORE DETAILS |
| ENST00000394376 | 11:64570996:64578766:-1 | MORE DETAILS |
| ENST00000394374 | 11:64570996:64578213:-1 | MORE DETAILS |
| ENST00000443283 | 11:64570996:64578188:-1 | MORE DETAILS |

DOWNLOAD HASH RESULTS (PATTERNED)

*FIG. 6-C*

| Cotmix | GENES | HASH ALGORITHM | HASH PATTERN | GENE INFO LIST | |
|---|---|---|---|---|---|
| GENE: MEN1 | | | | | |
| SUMMARY | TRANSCRIPT ID: | ENST00000377316 | | | |
| TRANSCRIPTS | SEQUENCE NAME: | 11:64570988.64577957:-1 | | | |
| | HASH RESULTS | | | | |
| | HASH ALGORITHM | RABIN-KARP | | | |
| | | | FORWARD | REVERSE | FORWARD + REVERSE |
| | | HASH STRING | HASH ON HASH | HASH STRING | HASH ON HASH |
| | DNA | DOWNLOAD | 862028147.0 | DOWNLOAD | 814704588.0 |
| | CDNA | DOWNLOAD | 934175297.0 | DOWNLOAD | 1067744487.0 | 999234394.0 |
| | INTRON | DOWNLOAD | 686613728.0 | DOWNLOAD | 859570310.0 | 985003842.0 |
| | CDS | DOWNLOAD | 738223483.0 | DOWNLOAD | 510783146.0 | 1014705374.0 |
| | CDS+INTRON | DOWNLOAD | 683380246.0 | DOWNLOAD | 693360450.0 | 1015075662.0 |
| | PROTEIN | DOWNLOAD | 546770841.0 | DOWNLOAD | 129836554.0 | 59639333.0 |
| | HASH ALGORITHM | RABIN-KARP-64 | | | |
| | | | FORWARD | REVERSE | FORWARD + REVERSE |
| | | HASH STRING | HASH ON HASH | HASH STRING | HASH ON HASH |
| | DNA | DOWNLOAD | 1851989373796352000 | DOWNLOAD | 4235867274522221440 | |
| | CDNA | DOWNLOAD | 3527238356944355328 | DOWNLOAD | 2130241786529906688 | 3889375944177090560 |
| | INTRON | DOWNLOAD | 2862228114438053376 | DOWNLOAD | 2366642550045343744 | 3085019007803195392 |
| | CDS | DOWNLOAD | 3170950990062026752 | DOWNLOAD | 2563609233698914304 | 5167057997913128960 |
| | CDS+INTRON | DOWNLOAD | 2054435122438340608 | DOWNLOAD | 3647239946067705856 | 4321391426360508416 |
| | PROTEIN | DOWNLOAD | | DOWNLOAD | | 4330077667657728 |
| | HASH ALGORITHM | MINHASH-FNV1-64 | | | |
| | | | FORWARD | REVERSE | FORWARD + REVERSE |

*FIG. 6-D*

Cotmix

- GENE: MEN1
- SUMMARY
- TRANSCRIPTS
- FRACTIONS

FRACTION OFFSET RESEARCH
- MEN1
- OFFSET
- [SEARCH]

| | GENES | HASH ALGORITHM | HASH PATTERN | FRACTION TESTS | PATTERN TESTS | RNA ENQUIRY | GENE INFO |
|---|---|---|---|---|---|---|---|

- GENE: MEN1
- WINDOW SIZE: 231880
- SEQUENCE DIRECTION: FORWARD
- HASH METHOD: FNV1-BITS64
- WINDOW OFFSET: 912
- PROTEIN ORDER PERCENTAGE: 80.0%
- GENE RANK: 3.8
- COMBINED RANK: 3.0

GENERATE FRACTIONS USING HALF OF CURRENT WINDOW SIZE. JOB WILL BE DONE AT BACKEND AND NOTICE EMAIL WILL BE SENT ONCE IT IS FINISHED.

EMAIL [ ]
[SPLIT WINDOW]

| TRANSCRIPT | INTRON OFFSET HASH VALUE | INTRON COVERED | INTRON ORDER | PROTEIN ORDER | PROTEIN HASH VALUE | GENE RANK INTRON ORDER | GENE RANK |
|---|---|---|---|---|---|---|---|
| ENST00000315422 | 3451312628255805824 | 1,2 | 1 | 12 | 13888077090689236035 | 1 | 11 |
| ENST00000450708 | 6281623717474987683 | 1,2 | 2 | 2 | 6743057925785323865 | 2 | 0 |

FIG. 6-E

| antx | GENES | HASH ALGORITHM | HASH PATTERN | FRACTION TESTS | | PATTERN TESTS | RNA ENQUIRY | GENE INFO |
|---|---|---|---|---|---|---|---|---|
| TRANSCRIPT | | INTRON OFFSET HASH VALUE | INTRON COVERED | INTRON ORDER | PROTEIN ORDER | PROTEIN HASH VALUE | GENE RANK INTRON ORDER | GENE RANK |
| ENST00000315422 | | 345131262855805824 | | | | | | |
| ENST00000450708 | | 6281623717474987683 | 1,2 | 1 | 12 | 13888077090689236035 | 1 | 11 |
| ENST00000440873 | | 7500087159562702031 | 1,2 | 2 | 2 | 6743057925785323865 | 2 | 0 |
| ENST00000377321 | | 7500087159562702031 | 1,2 | 3 | 3 | 9662452273227638168 | 3 | 0 |
| ENST00000394374 | | 7610640120683772611 | 1,2 | 4 | 9 | 10854016887269896695 | 3 | 6 |
| ENST00000337652 | | 9764873071974511583 | 1 | 5 | 4 | 10016473972116439183 | 5 | 1 |
| ENST00000429702 | | 9764873071974511583 | 1 | 6 | 4 | 10016473972116439183 | 6 | 2 |
| ENST00000424912 | | 10723298138492153529 | 1 | 7 | 10 | 12865572994853230352 | 6 | 4 |
| ENST00000394376 | | 10723298138492153529 | 1,2 | 8 | 10 | 12865572994853230352 | 8 | 2 |
| ENST00000377313 | | 12336626117277880197 | 1 | 9 | 4 | 10016473972116439183 | 8 | 4 |
| ENST00000443283 | | 13800979974043254785 | 1 | 10 | 4 | 10016473972116439183 | 10 | 6 |
| ENST00000312049 | | 13800979974043254785 | 1 | 11 | 4 | 10016473972116439183 | 11 | 7 |
| ENST00000377326 | | 15314606436471416474 | 1 | 12 | 12 | 13888077090689236035 | 11 | 1 |
| ENST00000377316 | | 15314606436471416474 | 1 | 13 | 12 | 13888077090689236035 | 13 | 1 |
| ENST00000413626 | | 16861191746261380102 | 1,2 | 14 | 1 | 1070273296197864103 | 13 | 12 |
| | | | | 15 | 15 | 15724440847510920542 | 15 | 0 |

| GENE: | MEN1 | | | | | |
|---|---|---|---|---|---|---|
| WINDOW SIZE: | 231880 | | | | | |
| SEQUENCE DIRECTION: | FORWARD | | | | | |
| HASH METHOD: | FNV1-BITS64 | | | | | |
| WINDOW OFFSET: | 912 | 2.28 | | | | |
| PROTEIN ORDER PERCENTAGE: | 60.0% | | | | | |
| GENE RANK: | 3.8 | | | | | |

| TRANSCRIPT | INTRON OFFSET HASH VALUE | INTRON ORDER | PROTEIN ORDER | PROTEIN HASH VALUE | GENE RANK INTRON ORDER | GENE RANK |
|---|---|---|---|---|---|---|
| ENST00000315422 | 3451312628255805824 | 1 | 12 | 13888077090689236035 | 1 | 11 |
| ENST00000450708 | 6281623717474987683 | 2 | 2 | 6743057925785323865 | 2 | 0 |
| ENST00000440873 | 7500087159562702031 | 3 | 3 | 9662452273227638168 | 3 | 0 |
| ENST00000377321 | 7500087159562702031 | 4 | 9 | 10854016887269896695 | 3 | 6 |
| ENST00000394374 | 7610640120683772611 | 5 | 4 | 10016473972116439183 | 5 | 1 |
| ENST00000337652 | 9764873071974511583 | 6 | 4 | 10016473972116439183 | 6 | 2 |
| ENST00000429702 | 9764873071974511583 | 7 | 10 | 12865572994853230352 | 6 | 4 |
| ENST00000424912 | 10723298138492153529 | 8 | 10 | 12865572994853230352 | 8 | 2 |
| ENST00000394376 | 10723298138492153529 | 9 | 4 | 10016473972116439183 | 8 | 4 |
| ENST00000377313 | 12336626117277880197 | 10 | 4 | 10016473972116439183 | 10 | 6 |
| ENST00000443283 | 13800979974043254785 | 11 | 4 | 10016473972116439183 | 11 | 7 |
| ENST00000312049 | 13800979974043254785 | 12 | 12 | 13888077090689236035 | 11 | 1 |
| ENST00000377326 | 15314606436471416474 | 13 | 12 | 13888077090689236035 | 13 | 1 |
| ENST00000377316 | 15314606436471416474 | 14 | 1 | 10702732961978641034 | 13 | 12 |
| ENST00000413626 | 16861191746261380102 | 15 | 15 | 15724440847510920542 | 15 | 0 |

| GENE: | MEN1 | | | | | |
|---|---|---|---|---|---|---|
| WINDOW SIZE: | 231880 | | | | | |
| SEQUENCE DIRECTION: | FORWARD | | | | | |
| HASH METHOD: | FNV1-BITS64 | | | | | |
| WINDOW OFFSET: | 890 | | | | | |
| PROTEIN ORDER PERCENTAGE: | 40.0% | | 1.2 | BEST FORWARD OFFSET | | |
| GENE RANK: | 3.0 | | | | | |

| TRANSCRIPT | INTRON OFFSET HASH VALUE | INTRON ORDER | PROTEIN ORDER | PROTEIN HASH VALUE | GENE RANK INTRON ORDER | GENE RANK |
|---|---|---|---|---|---|---|
| ENST00000450708 | 6327655304559821451 | 1 | 2 | 6743057925785323865 | 1 | 1 |
| ENST00000440873 | 7134725578693910305 | 2 | 3 | 9662452273227638168 | 2 | 1 |
| ENST00000377321 | 7134725578693910305 | 3 | 9 | 10854016887269896695 | 2 | 7 |
| ENST00000394374 | 7701976967603055507 | 4 | 4 | 10016473972116439183 | 4 | 0 |
| ENST00000394376 | 8109457222435681473 | 5 | 4 | 10016473972116439183 | 5 | 1 |
| ENST00000424912 | 8109457222435681473 | 6 | 10 | 12865572994853230352 | 5 | 5 |
| ENST00000377313 | 9215446792914690796 | 7 | 4 | 10016473972116439183 | 7 | 3 |
| ENST00000443283 | 9285000765253658576 | 8 | 4 | 10016473972116439183 | 8 | 4 |
| ENST00000312049 | 9285000765253658576 | 9 | 12 | 13888077090689236035 | 8 | 4 |
| ENST00000337652 | 10563335891101127798 | 10 | 4 | 10016473972116439183 | 10 | 6 |
| ENST00000429702 | 10563335891101127798 | 11 | 10 | 12865572994853230352 | 10 | 0 |
| ENST00000377316 | 14962010840217504753 | 12 | 1 | 10702732961978641 03 | 12 | 11 |
| ENST00000377326 | 14962010840217504753 | 13 | 12 | 13888077090689236035 | 12 | 0 |
| ENST00000315422 | 15315647993872179342 | 14 | 12 | 13888077090689236035 | 14 | 2 |
| ENST00000413626 | 15903205534756813581 | 15 | 15 | 15724440847510920542 | 15 | 0 |

Cotontex

GENE: MEN1
SUMMARY
TRANSCRIPTS
FRACTIONS

FRACTION OFFSET RESEARCH
MEN1
OFFSET
[SEARCH]

GENES | HASH ALGORITHM | HASH PATTERN | FRACTION TESTS | PATTERN TESTS | RNA ENQUIRY | GENE INFO LIST

GENE: MEN1
WINDOW SIZE: 231880
SEQUENCE DIRECTION: FORWARD
HASH METHOD: FNV1-BITS64
WINDOW OFFSET: 51631
PROTEIN ORDER PERCENTAGE: 80.0%
GENE RANK: 3.47
COMBINED RANK: 2.67

GENERATE FRACTIONS USING HALF OF CURRENT WINDOW SIZE. JOB WILL BE DONE AT BACKEND AND NOTICE EMAIL WILL BE SENT ONCE IT IS FINISHED.
EMAIL [         ]
[SPLIT WINDOW]

| TRANSCRIPT | INTRON OFFSET HASH VALUE | INTRON COVERED | INTRON ORDER | PROTEIN ORDER | PROTEIN HASH VALUE | GENE RANK INTRON ORDER | GENE RANK |
|---|---|---|---|---|---|---|---|
| ENST00000377313 | 16761306651774131 3 | 1 | 1 | 4 | 10016473972116439183 | 1 | 3 |
| ENST00000394374 | 25039618815126349 17 | 2 | 2 | 4 | 10016473972116439183 | 2 | 2 |

| GENES | HASH ALGORITHM | | FRACTION TESTS | PATTERN TESTS | RNA ENQUIRY | GENE INFO LIST | |
|---|---|---|---|---|---|---|---|
| TRANSCRIPT | INTRON OFFSET HASH VALUE | HASH PATTERN INTRON COVERED | INTRON ORDER | PROTEIN ORDER | PROTEIN HASH VALUE | GENE RANK INTRON ORDER | GENE RANK |
| ENST00000377313 | 1676130665177741313 | 1 | 1 | 4 | 10016473972116439183 | 1 | 3 |
| ENST00000394374 | 2503961881512634917 | ,2 | 2 | 4 | 10016473972116439183 | 2 | 2 |
| ENST00000394376 | 5164633206682038560 | ,2 | 3 | 4 | 10016473972116439183 | 3 | 1 |
| ENST00000424912 | 5164633206682038560 | ,2 | 4 | 10 | 12865572994853230352 | 3 | 7 |
| ENST00000429702 | 5819458165969913902 | 1 | 5 | 10 | 12865572994853230352 | 5 | 5 |
| ENST00000337652 | 5819458165969913902 | 1 | 6 | 4 | 10016473972116439183 | 5 | 1 |
| ENST00000443283 | 7189214929071588867 | 1,2 | 7 | 4 | 10016473972116439183 | 7 | 3 |
| ENST00000440873 | 9351644970681852145 | 1,2 | 8 | 3 | 9662452273227638168 | 8 | 5 |
| ENST00000377321 | 9351644970681852145 | 1,2 | 9 | 9 | 10854016887269896695 | 8 | 1 |
| ENST00000377316 | 9534319619692397952 | 1 | 10 | 1 | 10702732961978641103 | 10 | 9 |
| ENST00000377326 | 9534319619692397952 | 1 | 11 | 12 | 13888077090689236035 | 10 | 2 |
| ENST00000315422 | 12292542568658633110 | ,2 | 12 | 12 | 13888077090689236035 | 12 | 0 |
| ENST00000312049 | 15081914161581960811 | 1,2 | 13 | 12 | 13888077090689236035 | 13 | 1 |
| ENST00000450708 | 16379423582671150862 | 1,2 | 14 | 2 | 6743057925785323865 | 14 | 12 |
| ENST00000413626 | 18300401426631122607 | 1,2 | 15 | 15 | 15724440847510920542 | 15 | 0 |

Cobrotx  [GENES]  HASH ALGORITHM | HASH PATTERN | FRACTION TESTS | PATTERN TESTS | RNA ENQUIRY | GENE INFO LIST

GENE: MEN1
SUMMARY
TRANSCRIPTS
FRACTIONS

FRACTION OFFSET RESEARCH
- MEN1 ⬥
- OFFSET
- [SEARCH]

| | |
|---|---|
| GENE: | MEN1 |
| WINDOW SIZE: | 231880 |
| SEQUENCE DIRECTION: | REVERSE |
| HASH METHOD: | FNV1-BITS64 |
| WINDOW OFFSET: | 27 |
| PROTEIN ORDER PERCENTAGE: | 80.0% |
| GENE RANK: | 3.0 |
| COMBINED RANK: | 2.2 |

GENERATE FRACTIONS USING HALF OF CURRENT WINDOW SIZE. JOB WILL BE DONE AT BACKEND AND NOTICE EMAIL WILL BE SENT ONCE IT IS FINISHED.

EMAIL [         ]
[SPLIT WINDOW]

| TRANSCRIPT | INTRON OFFSET HASH VALUE | INTRON COVERED | INTRON ORDER | PROTEIN ORDER | PROTEIN HASH VALUE | GENE RANK INTRON ORDER | GENE RANK |
|---|---|---|---|---|---|---|---|
| ENST00000377316 | 3698158591125580096 | 1 | 1 | 1 | 3382694192351914659 | 1 | 0 |
| ENST00000450708 | 4355483256383501278 | 1, 2, 3 | 2 | 7 | 9227863736115087627 | 2 | 5 |

| GENES | HASH ALGORITHM | | HASH PATTERN | FRACTION TESTS | | PATTERN TESTS | | RNA ENQUIRY | GENE INFO LIST | |
|---|---|---|---|---|---|---|---|---|---|---|
| TRANSCRIPT | INTRON OFFSET HASH VALUE | | | INTRON COVERED | INTRON ORDER | PROTEIN ORDER | PROTEIN HASH VALUE | | GENE RANK INTRON ORDER | GENE RANK |
| ENST00000377316 | 369815859112558009 6 | | 1 | 1 | 1 | 1 | 338269419235191465 9 | | 1 | 0 |
| ENST00000450708 | 4355483256383501278 | | | 1,2,3 | 2 | 7 | 9227863736115087627 | | 2 | 5 |
| ENST00000377313 | 5495508876569419836 | | | 1,2 | 3 | 2 | 4639022252409589953 | | 3 | 1 |
| ENST00000394376 | 5495508876569419836 | | | 1,2 | 4 | 2 | 4639022252409589953 | | 3 | 1 |
| ENST00000443283 | 5495508876569419836 | | | 1,2 | 5 | 2 | 4639022252409589953 | | 3 | 1 |
| ENST00000394374 | 5495508876569419836 | | | 1,2 | 6 | 2 | 4639022252409589953 | | 3 | 1 |
| ENST00000337652 | 5495508876569419836 | | | 1,2 | 7 | 2 | 4639022252409589953 | | 3 | 1 |
| ENST00000377321 | 5495508876569419836 | | | 1,2 | 8 | 8 | 1023699925537766240 9 | | 3 | 5 |
| ENST00000377326 | 5495508876569419836 | | | 1,2 | 9 | 11 | 1759592625683578425 3 | | 3 | 8 |
| ENST00000315422 | 5495508876569419836 | | | 1,2 | 10 | 11 | 1759592625683578425 3 | | 3 | 8 |
| ENST00000312049 | 5495508876569419836 | | | 1,2 | 11 | 11 | 1759592625683578425 3 | | 3 | 8 |
| ENST00000440873 | 1088360883663953600 6 | | | 1 | 12 | 10 | 1679472542974690512 4 | | 12 | 2 |
| ENST00000413626 | 1276408734317814471 8 | | | 1,2 | 13 | 9 | 1346595966740626392 8 | | 13 | 4 |
| ENST00000424912 | 1577816298099945144 3 | | | 1 | 14 | 14 | 1840840903557431603 8 | | 14 | 0 |
| ENST00000429702 | 1577816298099945144 3 | | | 1 | 15 | 14 | 1840840903557431603 8 | | 14 | 0 |

| Cobnex | GENES | HASH ALGORITHM | HASH PATTERN | FRACTION TESTS | PATTERN TESTS | RNA ENQUIRY | GENE INFO LIST |

GENE: MEN1
SUMMARY
TRANSCRIPTS
FRACTIONS

FRACTION OFFSET RESEARCH

MEN1 ◆

OFFSET

[SEARCH]

GENE: MEN1
WINDOW SIZE: 231880
SEQUENCE DIRECTION: REVERSE
HASH METHOD: FNV1-BITS64
WINDOW OFFSET: 231870
PROTEIN ORDER PERCENTAGE: 53.33%
GENE RANK: 6.0
COMBINED RANK: 5.47

GENERATE FRACTIONS USING HALF OF CURRENT WINDOW SIZE. JOB WILL BE DONE AT BACKEND AND NOTICE EMAIL WILL BE SENT ONCE IT IS FINISHED.

EMAIL [        ]
[SPLIT WINDOW]

| TRANSCRIPT | INTRON OFFSET HASH VALUE | INTRON COVERED | INTRON ORDER | PROTEIN ORDER | PROTEIN HASH VALUE | GENE RANK | GENE RANK INTRON ORDER |
|---|---|---|---|---|---|---|---|
| ENST00000429702 | 4598621450107236996 | 1 | 1 | 14 | 18408409035574316038 | 1 | 13 |
| ENST00000440873 | 10979565776532699696 | 1, 2 | 2 | 10 | 16794725429746905124 | 2 | 8 |

| GENES | HASH ALGORITHM | HASH PATTERN | FRACTION TESTS | PATTERN TESTS | | RNA ENQUIRY | GENE INFO LIST | |
|---|---|---|---|---|---|---|---|---|
| TRANSCRIPT | INTRON OFFSET HASH VALUE | INTRON COVERED | INTRON ORDER | PROTEIN ORDER | PROTEIN HASH VALUE | | GENE RANK INTRON ORDER | GENE RANK |
| ENST00000429702 | 4598621450107236960 | 1 | 1 | 14 | 18408409035574316038 | | 1 | 13 |
| ENST00000440873 | 10979565577653269960 | 1,2 | 2 | 10 | 16794725429746905124 | | 2 | 8 |
| ENST00000450708 | 20086257606781953950 | ,3,4 | 3 | 7 | 9227863736115087627 | | 3 | 4 |
| ENST00000413626 | 20785739555654697400 | ,2 | 4 | 9 | 13465959667406263928 | | 4 | 5 |
| ENST00000424912 | 6598178738853493497 | 1 | 5 | 14 | 18408409035574316038 | | 5 | 9 |
| ENST00000377313 | 7737664465932464792 | ,2,3 | 6 | 2 | 4639022252409589953 | | 6 | 4 |
| ENST00000394376 | 7737664465932464792 | ,2,3 | 7 | 2 | 4639022252409589953 | | 6 | 4 |
| ENST00000443283 | 7737664465932464792 | ,2,3 | 8 | 2 | 4639022252409589953 | | 6 | 4 |
| ENST00000394374 | 7737664465932464792 | ,2,3 | 9 | 2 | 4639022252409589953 | | 6 | 4 |
| ENST00000337652 | 7737664465932464792 | ,2,3 | 10 | 2 | 4639022252409589953 | | 3 | 4 |
| ENST00000377321 | 7737664465932464792 | ,2,3 | 11 | 8 | 10236999255377662409 | | 6 | 2 |
| ENST00000315422 | 7737664465932464792 | ,2,3 | 12 | 11 | 17595926256835784253 | | 6 | 5 |
| ENST00000377326 | 7737664465932464792 | ,2,3 | 13 | 11 | 17595926256835784253 | | 6 | 5 |
| ENST00000312049 | 7737664465932464792 | ,2,3 | 14 | 11 | 17595926256835784253 | | 6 | 5 |
| ENST00000377316 | 8278693811354967333 | 1 | 15 | 1 | 3382694192351914659 | | 15 | 14 |

| TRANSCRIPT | INTRON OFFSET HASH VALUE | INTRON COVERED | INTRON ORDER | PROTEIN ORDER | PROTEIN HASH VALUE | GENE RANK INTRON ORDER | GENE RANK |
|---|---|---|---|---|---|---|---|
| ENST00000377313 | 1676130665177741313 | 1 | 1 | 4 | 10016473972116439183 | 1 | 3 |
| ENST00000394374 | 2503961881512634917 | 1,2 | 2 | 4 | 10016473972116439183 | 2 | 2 |
| ENST00000394376 | 5164633206682038560 | 1,2 | 3 | 4 | 10016473972116439183 | 3 | 1 |
| ENST00000424912 | 5164633206682038560 | 1,2 | 4 | 10 | 12865572994853230352 | 3 | 7 |
| ENST00000429702 | 5819545816596913902 | 1 | 5 | 10 | 12865572994853230352 | 5 | 5 |
| ENST00000337652 | 5819545816596913902 | 1 | 6 | 4 | 10016473972116439183 | 5 | 1 |
| ENST00000443283 | 7189214929071588867 | 1,2 | 7 | 4 | 10016473972116439183 | 7 | 3 |
| ENST00000440873 | 9351644970681852145 | 1,2 | 8 | 3 | 9662452273227638168 | 8 | 5 |
| ENST00000377321 | 9351644970681852145 | 1,2 | 9 | 9 | 10854016887269896695 | 8 | 1 |
| ENST00000377316 | 9534311961692397952 | 1 | 10 | 1 | 10702732961978641103 | 10 | 9 |
| ENST00000377326 | 9534311961692397952 | 1 | 11 | 12 | 13888077090689236035 | 10 | 2 |
| ENST00000315422 | 12292542568658633110 | 1,2 | 12 | 12 | 13888077090689236035 | 12 | 0 |
| ENST00000312049 | 15081914161581960811 | 1,2 | 13 | 12 | 13888077090689236035 | 13 | 1 |
| ENST00000450708 | 16379423582671150862 | 1,2 | 14 | 2 | 6743057925785323865 | 14 | 12 |
| ENST00000413626 | 18300401426631122607 | 1,2 | 15 | 15 | 15724440847510920542 | 15 | 0 |

*FIG. 6-P*

SYSTEMS, METHODS, AND DEVICES FOR ANALYSIS OF GENETIC MATERIAL

RELATED APPLICATIONS

This application is a continuation of PCT/US2015/030478, filed May 13, 2015, which claims priority from (i) U.S. Provisional Patent Application No. 61/993,846, filed May 15, 2014; and (ii) U.S. Provisional Patent Application No. 62/015,492, filed Jun. 22, 2014, the entire contents of which are hereby fully incorporated herein by reference for all purposes.

SEQUENCE LISTING

The instant application contains a Sequence Listing which has been submitted electronically in ASCII format and is hereby incorporated by reference in its entirety. Said ASCII copy, created on May 26, 2016, is named 4040-0006_SL.txt and is 603 bytes in size.

COPYRIGHT STATEMENT

This patent document contains material subject to copyright protection. The copyright owner has no objection to the reproduction of this patent document or any related materials in the files of the United States Patent and Trademark Office, but otherwise reserves all copyrights whatsoever.

SOURCE CODE APPENDIX

This application includes a source code appendix with example computer source code. The source code appendix is considered part of this application for all purposes.

FIELD OF THE INVENTION

This invention relates to genetic engineering and microbiology, and, more particularly, to systems, methods, and devices for analysis of genetic material such as nucleotide sequences.

BRIEF DESCRIPTION OF THE DRAWINGS

Objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification.

FIG. 5-C shows aspects of protein coding (figure discloses SEQ ID NO: 1);

FIGS. 6-G to 6-P are screen shots of additional aspects of a web-based tool according to exemplary embodiments hereof.

DETAILED DESCRIPTION OF THE PRESENTLY PREFERRED EXEMPLARY EMBODIMENTS

Glossary and Abbreviations

Figure 1:
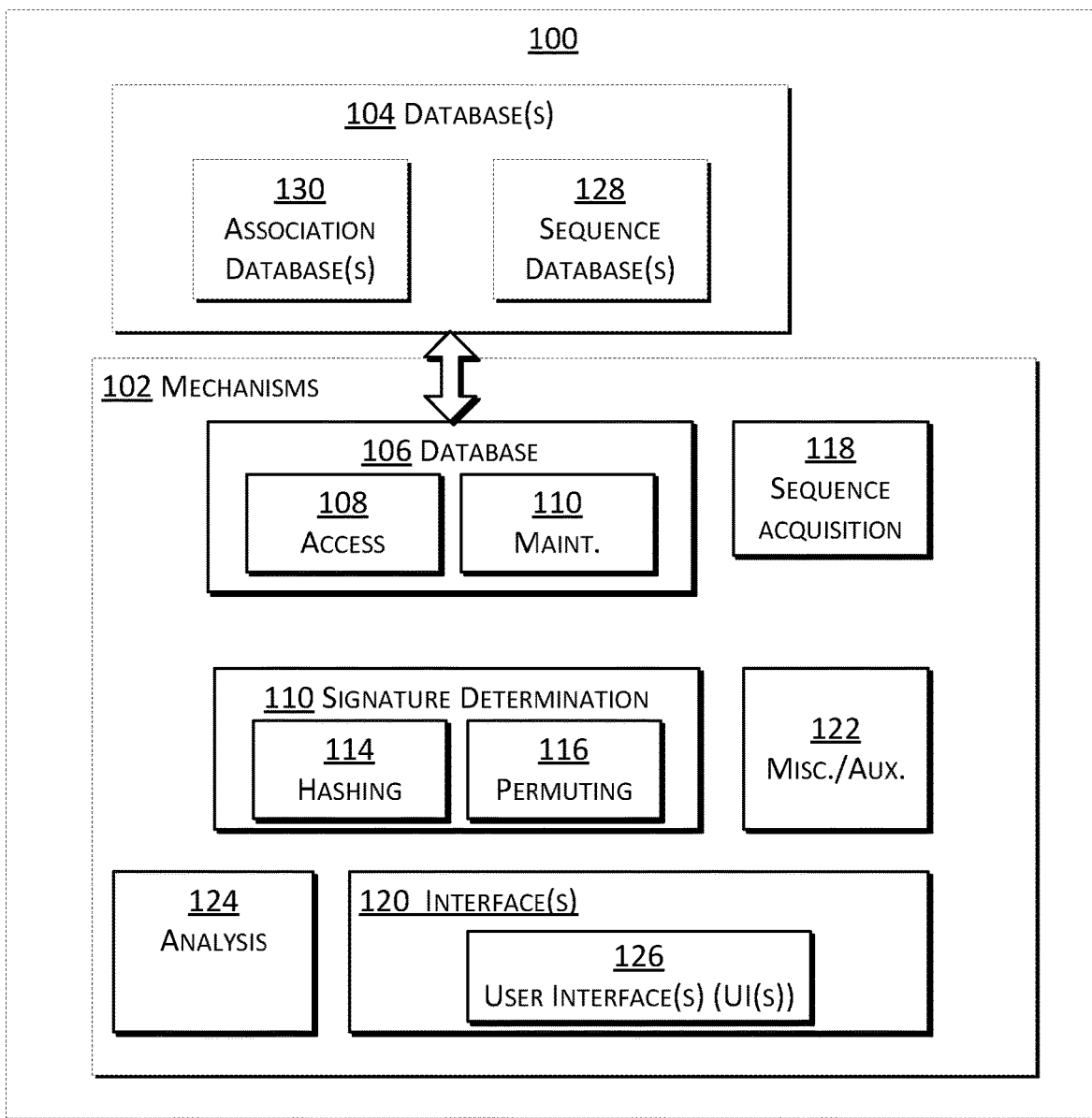
FIG. 1 shows an overview of a system according to embodiments hereof.

As used herein, unless used or described otherwise, the following terms or abbreviations have the following meanings:

"alphanumeric" means consisting of or using both letters and numbers;

"alphanumeric character" means a character that is either a letter or a number;

"alphanumeric string" means a character string consisting of letters and/or numbers;

"DNA" means deoxyribonucleic acid;

"DNA sequence" means a representation of the order in which the nucleotide bases are arranged within a nucleic acid sequence;

"exon" means a segment of a DNA or RNA molecule containing information coding for a protein or peptide sequence;

"FNV" means the Fowler-Noll-Vo hash function;

"genome" means the nuclear or organellar DNA content of a biological individual or sample;

"intron" means the part of a nucleotide sequence that's not an exon;

"RNA" means ribonucleic acid.

DESCRIPTION

Background and Overview

A DNA sequence is a sequence of nucleotide bases selected from the four nucleotide bases adenine (A), cytosine (C), guanine (G), and thymine (T). For notational convenience, and following convention, these bases are abbreviated herein as A, C, G, and T. That is, a DNA sequence S may be written as $s_1 s_2 \ldots s_k$, wherein each element $s_1$ in the sequence is selected from the set $\{A, C, T, G\}$.

As is well known, within the nucleus of a cell a DNA sequence takes the form of a double helix formed with base pairs. Within the base pairs, an adenine (A) nucleotide pairs with a thymine (T) nucleotide (and vice versa) and a cytosine (C) nucleotide pairs with a guanine (G) nucleotide (and vice versa).

As conventionally understood, a DNA sequence encodes a genetic function, and a DNA sequence may contain a gene, e.g., encoding for a protein.

There are twenty (20) amino acids (alanine, arginine, asparagine, aspartate, cysteine, glutamate, glutamine, glycine, histidine, isoleucine, leucine, lysine, methionine, phenylalanine, proline, serine, threonine, tryptophan, tyrosine, and valine) and all proteins are formed from combinations of these amino acids.

In order for a cell to perform a genetic function encoded in DNA (i.e., in a gene of the DNA) a copy of a portion of the DNA is made or transcribed onto messenger RNA (mRNA) to be passed from the nucleus into the cell. Transcription need not (and usually does not) read or copy the entire DNA, only the parts within the DNA that hold the information to perform the required function—e.g., to make the desired protein. In the case of protein production, a starting point is found in the DNA for the desired protein and then a transcript of the DNA is made (using RNA) up to an end point in the DNA.

The RNA copies at least a portion of the DNA using complementary bases according to the following rules:

| DNA | to | RNA |
|---|---|---|
| T | → | A |
| C | → | G |
| G | → | C |
| A | → | U |

Note that on the RNA the complement of A is U (Uracil), not thymine (T).

Thus an RNA sequence R may be written as $r_1 r_2 \ldots r_k$, wherein each $r_i$ is selected from the set $\{A, C, U, G\}$.

When DNA is transcribed to RNA each "T" is replaced by a "U", otherwise the sequence remains the same.

Before being sent from the nucleus into the cytoplasm of the cell, the RNA may undergo further processing, as explained here.

Recall that each gene may code for a specific protein and that the DNA that makes up a gene provides the code. However, not all of the DNA within a gene may directly code for proteins. The parts of DNA that codes directly for proteins are called exons. Non-coding portions of DNA that are within a gene and are between exons (coding portions) are referred to as introns. A gene may thus comprise one or exons interspersed with one or more introns. (E.g., as shown in the following:

<EXON$_1$><INTRON$_1$><EXON$_2$><INTRON$_2$>
<EXON$_3$><INTRON$_4$><EXON$_4$>

Processing of the transcribed RNA in the nucleus removes the introns so that the messenger RNA (mRNA) only contains the exons for a gene. E.g., for the above example, the mRNA would consist of:

<EXON-T$_1$><EXON-T$_2$><EXON-T$_3$><EXON-T$_4$> where <EXON-T$_k$> is the RNA sequence corresponding to the DNA sequence <EXON$_k$>.

The mRNA comprising the gene's concatenated exons is passed out of the cell's nucleus to the cytoplasm where translation of the mRNA to a protein occurs. Specifically, once the mRNA is made from transcription, the mRNA moves from the cell's nucleus into the cytoplasm where a ribosome assembles amino acids associated with another molecule known as tRNA that match the codon of mRNA sequences moving through the ribosome (as specified or encoded in the mRNA) according to the following process.

The bases in an RNA sequence may conveniently be grouped into triples called codons. As conventionally understood, one triple or codon—the first codon of the mRNA transcript—encodes a start codon. The most common start codon is AUG. A stop codon (or termination codon) is a nucleotide triplet within mRNA that signals termination of translation. There are several stop codons, specifically, in RNA: UAG, UAA, and UGA (in DNA: TAG, TAA, TGA).

Each codon (other than the start and stop codons) corresponds to one of the twenty amino acids (recall that there are twenty (20) amino acids and all proteins are formed from combinations of these amino acids). As there are four bases, there are sixty four possible codons (i.e., there are 64 triples that can be formed from the bases A, C, G, T (or A, C, G, U). As there are 20 amino acids and 64 possible codons that code for amino acids (less the start and stop codons), some amino acids are produced by more than one codon. For example, as shown in the table below, the four mRNA codons CCU, CCC, CCA, CCG all correspond to the amino acid proline. Similarly, the four mRNA codons GCU, GCC, GCA, GCG all correspond to the amino acid alanine. Notably, as discussed below with reference to FIG. 5-B, these codons differ only in their third nucleotide.

Translation from codon to protein occurs as follows:
1. In the cell's cytoplasm a ribosome recognizes the start codon in the mRNA and reads the mRNA one codon at a time.
2. An amino acid (one of the twenty) attached to an available tRNA molecule in the Cytoplasm is attracted by the ribosome and joined to form a sequence of amino acids based on the underlying mRNA codon's being processed through the ribosome, according to the rules in the following table, until a "stop" codon (ATG, ATT, ACT for DNA or UAA, UAG, UGA for RNA) is reached.

| Amino Acid | DNA Base Triplets | M-RNA Codons |
|---|---|---|
| Alanine | CGA, CGG, CGT, CGC | GCU, GCC, GCA, GCG |
| Arginine | GCA, GCG, GCT, GCC TCT, TCC | CGU, CGC, CGA, CGG AGA, AGG |
| asparagine | TTA, TTG | AAU, AAC |
| aspartate | CTA, CTG | GAU, GAC |
| Cysteine | ACA, ACG | UGU, UGC |
| glutamate | CTT, CTC | GAA, GAG |
| glutamine | GTT, GTC | CAA, CAG |
| glycine | CCA, CCG, CCT, CCC | GGU, GGC, GGA, GGG |
| histidine | GTA, GTG | CAU, CAC |
| isoleucine | TAA, TAG, TAT | AUU, AUC, AUA |
| leucine | AAT, AAC, GAA, GAG GAT, GAC | UUA, UUG, CUU, CUC CUA, CUG |
| lysine | TTT, TTC | AAA, AAG |
| methionine | TAC | AUG |
| phenylalanine | AAA, AAG | UUU, UUC |
| proline | GGA, GGG, GGT, GGC | CCU, CCC, CCA, CCG |
| serine | AGA, AGG, AGT, AGC TCA, TCG | UCU, UCC, UCA, UCG AGU, AGC |
| stop | ATG, ATT, ACT | UAA, UAG, UGA |
| threonine | TGA, TGG, TGT, TGC | ACU, ACC, ACA, ACG |
| tryptophan | ACC | UGG |
| tyrosine | ATA, ATG | UAU, UAC |
| valine | CAA, CAG, CAT, CAC | GUU, GUC, GUA, GUG |

The System

With reference now to FIG. 1, a system 100 according to embodiments hereof includes a number of mechanisms 102 interacting with one or more databases 104.

As used herein, the term "mechanism" refers to any device(s), process(es), service(s), or combination thereof. A mechanism may be implemented in hardware, software, firmware, using a special-purpose device, or any combination thereof. A mechanism may be integrated into a single device or it may be distributed over multiple devices. The various components of a mechanism may be co-located or distributed. The mechanism may be formed from other mechanisms. In general, as used herein, the term "mechanism" may thus be considered to be shorthand for the term device(s) and/or process(es) and/or service(s).

The exemplary mechanisms 102 may include database mechanism(s) 106, including database access mechanism(s) 108 and database maintenance mechanism(s) 110, signature determination mechanism(s) 112, which may include hashing mechanism(s) 114 and permuting mechanism(s) 116. Additionally, the mechanisms 102 may include sequence acquisition mechanism(s) 118, interface mechanism(s) 120, miscellaneous and auxiliary mechanism(s) 122, and analysis mechanism(s) 124. The interface mechanism(s) 120 may include user interface (UI) mechanism(s) 126.

The databases 104 may include one or more sequence databases 128 and one or more association databases 130.

Figure 2:
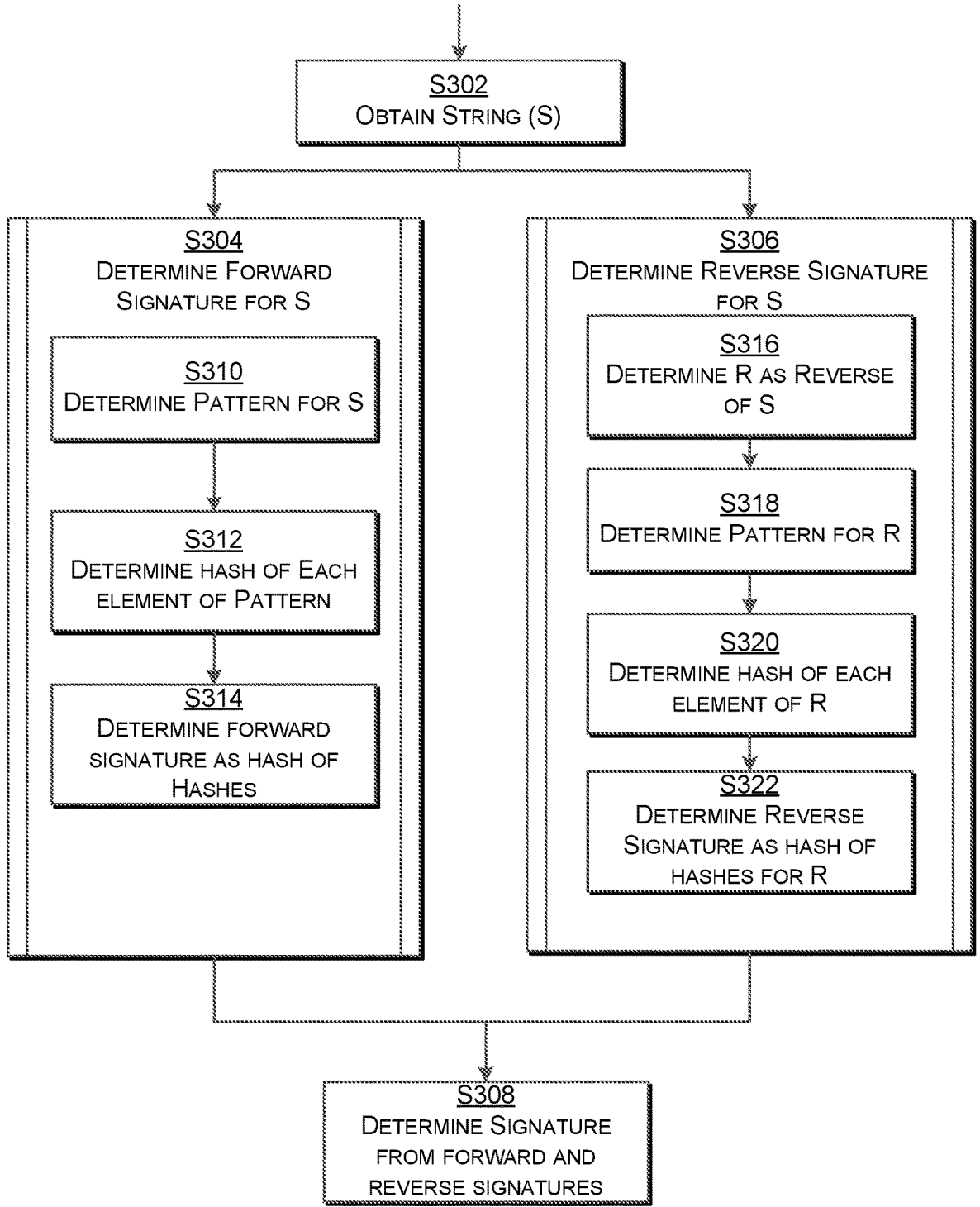
FIGS. 2-A and 2-B show exemplary database organizations according to embodiments hereof.

With reference now to FIGS. 2-A and 2-B, the sequence database(s) 128 may include a mapping of sequence identifiers to corresponding sequences such as DNA sequences, RNA sequences, proteins, or the like. The sequences may correspond to introns or exons. The sequence identifiers may be arbitrarily assigned by the system.

The association database(s) 130 preferably include a mapping of signatures (described in greater detail below) to associated and corresponding DNA sequences (e.g., as identified by their sequence identifiers). The signatures may also map to one or more of: (i) one or more intron sequences (e.g., as identified by their sequence identifiers), (ii) one or more exon sequences (e.g., as identified by their sequence identifiers), and (iii) a protein. It should be appreciated that a particular signature may not map to all of the fields. It should also be appreciated that the database may include other mappings, e.g., from intron signatures to genetic functions or the like. The protein, if included, may be identified by a protein identifier that maps to a separate protein database (not shown) or it may be identified by a sequence identifier, mapping to the sequence database 128.

In the exemplary mappings in FIGS. 2-A and 2-B, the k-th row shows that signature Sk maps to DNA sequence identified by sequence identifier IDk (that maps to a DNA sequence in the sequence database 128 in FIG. 2-B). Signature Sk may also map to (i) a sequence of one or more introns (identified by a corresponding one or more sequence identifiers ID-I-k . . . ); (ii) a sequence of one or more exons (identified by a corresponding one or more sequence identifiers ID-E-k . . . ); and (iii) a protein (identified by a corresponding sequence identifier Pk).

In FIGS. 2-A and 2-B the mappings are shown as tables. Those of ordinary skill in the art will realize and appreciate, upon reading this description, that these are merely exemplary representations of the databases and their mappings, and that different and/or other database organizations and/or representations may be used. It should be appreciated that the system is not limited by the particular database implementation or organization.

Data Representation

For computational purposes, e.g., in order to record and manipulate nucleotide (DNA and RNA) sequences, genetic sequencing data representing nucleotide sequences or peptide sequences are typically stored in a text format, such as FASTA or FASTQ, using single-letter codes to represent the nucleotides or amino acids. In the FASTA format, the bases adenine (A), cytosine (C), guanine (G), and thymine (T) are represented by the four ASCII letters "A", "C", "G", and "T", respectively. For RNA the base thymine (T) is replaced by the base uracil (U), represented by the letter "U". Thus the nucleotides that constitute DNA and RNA may be expressed in five distinct characters (A, G, C, T, or U for adenine, guanine, cytosine, thymine, or uracil, respectively).

However, if space and storage requirements are a concern, 3 bits may be used to represent each character.

As there are five values to be considered in each type of sequence, 3 bits are sufficient to store each sequence element (i.e., each nucleotide).

For some computational purposes a DNA (or RNA) sequence may be considered to be a character string with the characters selected from (and limited to) "A", "C", "G", and "T" (or "U" instead of "T" for RNA).

In conventional programming languages, such sequences may be represented as strings of characters.

Since arithmetic functions will be performed on these strings (e.g., to compute their hashes), each letter may also be assigned a numeric value. It should be appreciated that standard encoding of values for the letters (e.g., ASCII) may be used, as long as the encoding is consistent across the system. In some embodiments the letters may be assigned the values, e.g., 1, 2, 3, 4, and 5 for the letters "A", "C", "G", "T", and "U", respectively. In these embodiments the DNA sequence "AAGCGT" would correspond to the numerical sequence (or number) "113234", whereas the RNA sequence "AAGCGU" would correspond to the numerical sequence (or number) "113235". Using this approach, a DNA or RNA sequence may be directly manipulated and operated on arithmetically. Those of ordinary skill in the art will realize and appreciate, upon reading this description, that different and/or other encodings of DNA and RNA sequences may be used, and that some of these encodings will provide more efficient storage than others, and that some of these encodings will provide more efficient computation than others. It should also be appreciated that different coding and storage schemes may be used for different aspects of the system, again, as long as consistency is maintained. For example, it may be efficient to store data in one form and to operate on those data in another form. Those of ordinary skill in the art will understand how to select an encoding scheme that balances storage and computing requirements.

By convention the 20 amino acids are sometimes identified by their first three letters (e.g., "glu" for "glutamine", etc.), although for storage and computation purposes they are typically given one-letter abbreviations. The following table shows the standard 3 and 1 letter abbreviations for the twenty amino acids.

| Amino Acid | 3-Letter | 1-Letter |
| --- | --- | --- |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Thus, as with DNA and RNA sequences, a protein may be represented by a character string (e.g., with the letters drawn from the alphabet in the 1-letter column in the table above). In order to operate arithmetically on sequences that represent proteins, each of the twenty characters may be assigned a different numeric value (e.g., 1 to 20 or the characters ASCII numeric value or some other value).

Determining a Sequence Signature

As noted above, the system 100 may store mappings or associations between signatures of sequences for different sequences or for sequences representing different physical entities. For example, the system 100 preferably stores one or more mappings of intron signatures to protein sequences (and/or their signatures). The signature determination mechanism(s) 110 include one or more mechanisms for determining a signature of a sequence.

In presently preferred implementations the signature ($V_S$) for a particular sequence (represented, e.g., as a character string $S=s_1s_2 \ldots s_n$) is obtained as follows:

Step 1: Obtain string $S=S_1S_2 \ldots S_n$

Step 2: Generate sequence (or ordered list) of substrings of S using a pattern function (described in greater detail below)

Step 3: Generate sequence of hash values, one for each element of the ordered list of substrings.

Step 4: Generate signature $F_S$ as a function of the sequence of hash values of the substrings. Preferably the signature $F_S$ is a hash of the concatenated sequence of hash values of the substrings.

Step 5: Repeat steps 2 to 4 for the reverse (R) of string S to obtain a signature $R_S$ of the reverse string R.

Step 6: Generate $V_S$ as a function of $F_S$ and $R_S$ (e.g., $F_S+R_S$)

Where the sequence S corresponds to an intron, the value $V_S$=signature (S) is a signature for that intron.

Where the sequence S corresponds to an exon, the value $V_S$=signature (S) is a signature for that exon.

Where the sequence S corresponds to a plurality of introns in a gene, the value $V_S$ is an intron signature for that gene. For example, suppose a gene has the form:

<EXON$_1$><INTRON$_1$><EXON$_2$><INTRON$_2$>
<EXON$_3$><INTRON$_3$><EXON$_4$>

Then the introns for that gene are: <INTRON$_1$><INTRON$_2$><INTRON$_3$> and $V_S$=signature (<INTRON$_1$><INTRON$_2$><INTRON$_3$>) may be considered an intron signature of the gene.

As is well known, a hash function is a function that converts its input into a numeric value, called its hash value. Preferably the hash function is a non-cryptographic hash function such as FNV (e.g., FNV1-64 Bit). Exemplary source code for the FNV hashing function (in the Ruby programming language) is shown in Appendix I, which is considered part of this application for all purposes.

For example, using the exemplary FNV source code in Appendix I, the function call puts FNV.calculate("AB-CDE") generates the hash value 8130071842065240010 corresponding to the string "ABCDE".

It should be appreciated that any hash function may be used, and that FNV is merely provided by way of example. Furthermore, while any hash function may be used, preferred embodiments hereof use two-way or reversible hash functions. In preferred embodiments the same hash function must be used for all independent entities in the string to produce the result.

The Pattern Function

For a given sequence S, a pattern function pattern(S) generates a sequence of substrings of $S=s_1s_2 \ldots s_n$ that, inter alia, preserve sequences between letters in the original string S. The sequence of substrings is preferably ordered and preferably includes all substrings S' of S (including S itself) where the characters in the substring S' are directly adjacent in S in the forward direction (i.e., from $s_1$ to $s_n$). In addition, the function pattern(S) preferably includes the reverse of the substrings S'. Thus, e.g., if "$s_1s_2$" is one of the S' substrings, then its reverse "$s_2s_1$" is also included by the pattern function.

As an example, pattern("123456") is given by the ordered list or sequence below (with elements separated for convenience by the bar character "|")

1|2|*21*|12|3|*32*|*23*|*321*|123|4|*43*|34|*432*|234|*4321*|1234|5|*54*|
45|*543*|345|*5432*|2345|*54321*|12345|6|*65*|56|*654*|456|*6543*|
3456|*65432*|23456|*654321*|123456

In the example above, merely to aid in this description, the forward substrings are underlined and the reverse substrings are shown in italics. A single character substring may be considered forward or backward, but is not repeated.

Exemplary source code for a pattern generating function (in the Ruby programming language) is shown in Appendix I hereto (the source code appendix). As an example, using that example code:
PatternHandler.generate_pattern("ATCGTA") generates the pattern:

A | T | TA | AT | C | CT | TC | CTA | ATC | G | GC | CG | GCT | TCG | GCTA |

ATCG | T | TG | GT | TGC | CGT | TGCT | TCGT | TGCTA | ATCGT | A | AT |

TA | ATG | GTA | ATGC | CGTA | ATGCT | TCGTA | ATGCTA | ATCGTA

It should be appreciated that although the pattern herein are described for some preferred embodiments, other patterns that preserve sequences between letters can vary. For example the forward pattern for the string 123 in some embodiments is 1|2|21|12|3|32|23|321|123, but the pattern 1|2|12|21|3|23|32|123|321 may be used in another embodiment.

Figure 3:
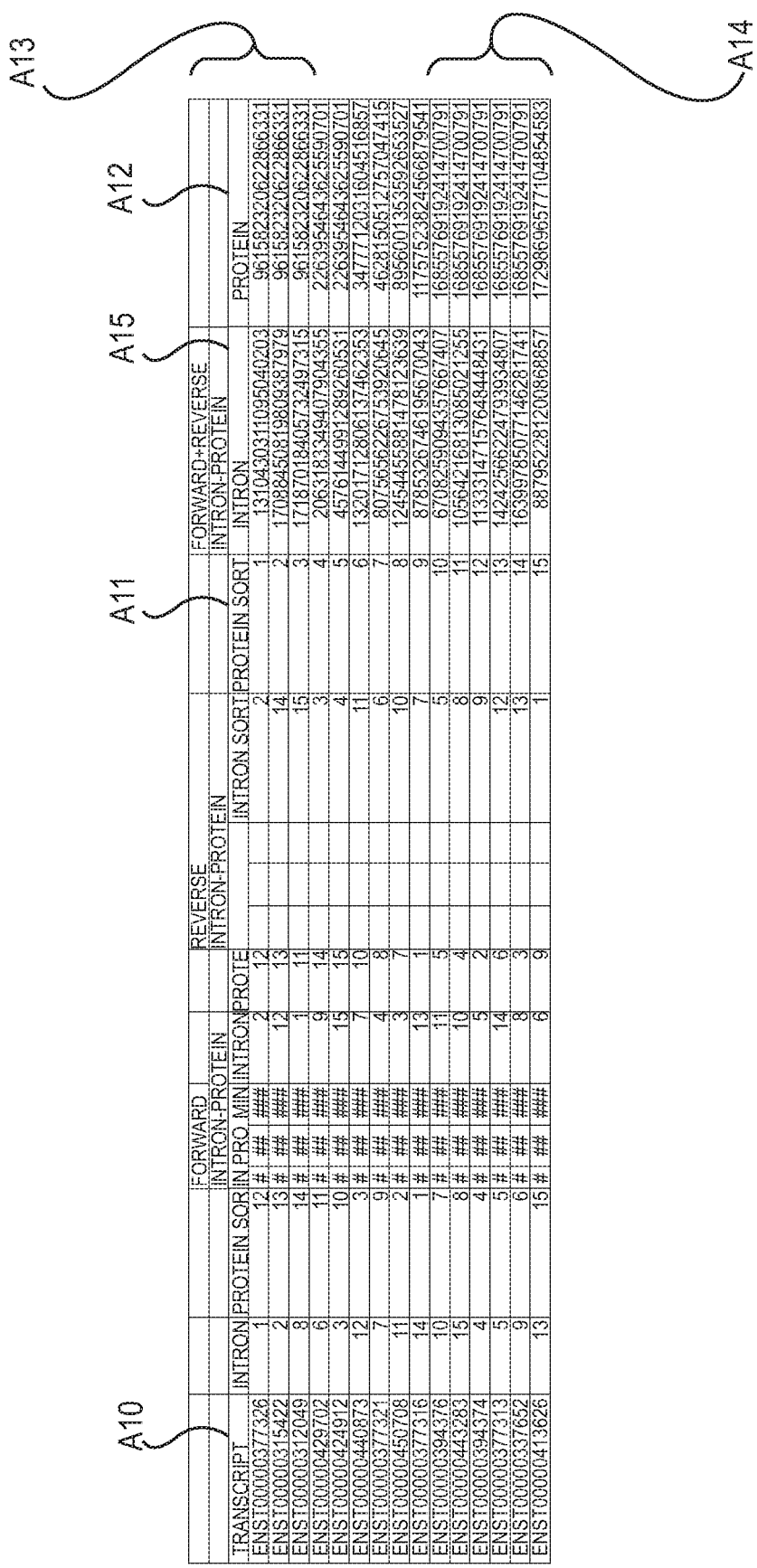
FIG. 3-A is a flow chart of processes according to embodiments hereof.

FIG. 3-A shows a flowchart of an exemplary signature calculation according to embodiments hereof. As shown in FIG. 3-A, first a string S is obtained (at S302). The string S may be an alphanumeric representation of a DNA sequence, a cDNA sequence, one or more introns, CDS, CDS with intron(s), or protein. It should be appreciated that the coding that the string uses will depend on the underlying physical object that the string represents. For example, as is well known, a DNA sequence will be represented by the four letter A, C, G, T, whereas an RNA sequence will be represented by the four letters A, C, G, U. Those of ordinary skill in the art will realize and appreciate, upon reading this description, that any encoding may be used for a sequence of a particular type (i.e., a sequence representing a particular type of physical item, as long as the same encoding is used throughout the system for entities of that type.

Having obtained the string S (at S302), the system then proceeds to determine a forward signature for S (at S304) and a signature for the reverse of S, denoted R (at S306). As noted above, a particular implementation may not use both forward and reverse signatures, although this is preferred. The forward and reverse signatures may be determined in series or in parallel. In some implementations or embodiments, the signature may be determined based on a string S' formed from S and the reverse of S.

As shown in FIG. 3-A, the forward signature for S may be determined (at S304) by determining a pattern for S (the pattern preferably comprising a plurality a substrings of S) (at S310), applying a function (e.g., a hash function) to each element of the pattern (at S312), and then determining the forward signature of S (at S314) by applying a function (e.g., a hash function) to the values determined in S312. As will be appreciated, when the functions applied in S312 and S314 are both hash functions then the forward signature of S is determined as a hash of hash values (at S314).

The reverse signature for S may be determined (at S306) by determining a string R as the reverse string of S (at S316), then determining a pattern for R (at S318), and then determining the reverse signature of S by applying a function (e.g., a hash function) to each element of the pattern (at S320) and then applying a function (e.g., a hash function) to the values (e.g., hash values) determined at S320. As will again be appreciated, when the functions applied in S320 and S322 are both hash functions then the reverse signature of S is determined as a hash of hash values (at S322).

Although various acts are shown in the flow diagram as being processed in series, those of ordinary skill in the art will realize and appreciate, upon reading this description, that some or all of the acts may be performed in parallel or at least partially in parallel.

The patterns determined for S and R (at S310 and S318, respectively) may, for example, be generated by the exemplary pattern function shown in the Appendix hereto.

DISCUSSION

For a sequence S of size n the function perm(S) returns permutations of the elements in S containing one or more elements. For example, for the sequence $S = s_1 s_2 s_3$, perm(S)=perm($s_1 s_2 s_3$) corresponds to the elements shown here listed separated by the character "|":

$s_1 | s_2 | s_1 s_2 | s_3 | s_2 s_3 | s_1 s_2 s_3$

For a sequence S of size n, define the function substrings (S) to be the subset of perm(S) that are either (i) single characters; or (ii) contiguous substrings of S. Note that the string S is considered a substring of itself.

So, e.g., while perm("ABCD") includes: A, AB, ABC, ABCD, ABD, ACD, AC, AD, B, BC, BCD, BD, C, CD Substrings("ABCD") consists of: A, AB, ABC, ABCD, B, BC, BCD, C, CD, D.

Note that the Substrings(S) does not include any substrings of the string that are not contiguous and directly adjacent in the original string S. So, e.g., "AC" and "AD" are not members of substrings("ABCD") as they are not directly adjacent in "ABCD".

For the sake of notation, the i-th element of Substrings(S) is referred to as $P_i$. These substrings may be stored in a data structure such as an array or a linked list or the like.

For a sequence $S = s_1 s_2 \ldots s_k$, define the function reverse (S) as: reverse($s_1 s_2 \ldots s_k$) = $s_k s_{k-1} \ldots s_2 s_1$ That is, reverse(S) produces the reverse of the sequence S. For example, for the sequence S="ATG", reverse(S)=reverse("ATG")="GTA", and substring(reverse(S))=substring("GTA")=G|T|GT|A|TA|GTA, whereas substring("ATG")=A|T|AT|G|TA|GTA Define a second substring function Substrings2(S) to be (i) Substrings(S); and (ii) reverse(Q) for each substring Q in Substrings(S). Thus, e.g., Substings2("ABCD")=A|B-|BA|AB|C|CB|BC|CBA|ABC|D|DC|CD|DCB|BCD|D-CBA|ABCD An exemplary signature function for a sequence S (Signature(S)) of length n is defined as follows:

1. Form a sequence S'=substrings2(S).
2. For each element $S'_j$ in S' determine a corresponding value $H_j = H(S'_j)$ for some function H. Note that each $S'_j$ is also a string (with one or more characters). This produces m values $H_1, H_2 \ldots H_{m-1}, H_m$. Preferably the function H is a hash function, more preferably a non-cryptographic hash function such as FNV (e.g., FNV1-64 Bit).

Upon completion of step 2, a list of m values will have been produced. These m values may be stored in a data structure such as an array or a linked list or the like.

3. The m values are concatenated to form a single value: $H_1 H_2 \ldots H_{m-1} H_m$ and a second function F is applied to this value:

V1=F($H_1 H_2 \ldots H_{m-1} H_m$)

Preferably the function F is also a hash function, and more preferably F is a non-cryptographic hash function such as FNV or the like. It should again be appreciated that any hash function may be used, and that FNV is merely provided by way of example.

The function F may be the same as the function H. That is, e.g., both F and H may be the same function. It should be appreciated that in cases where both F and H are hash functions, the value produced by F is computed as a hash of hash values.

In some embodiments the value V1 produced by F may be considered a signature for the sequence S. In some other embodiments, additional processing may be performed as follows:

4. Form a second sequence R=substrings2(reverse(S))
5. For each element $R_j$ in R determine a corresponding value $H'_j = H(R_j)$ for the function H. This produces m values $H'_1, H'_2 \ldots H'_{m-1}, H'_m$.
6. The m values are concatenated to form a single value: $H'_1 H'_2 \ldots H'_{m-1} H'_m$ and the second function F is applied to this value:

V2=F($H'_1 H'_2$

7. Determine V=G(V1, V2), where G is a function such as a hash function. Thus, effectively, V=F($H_1 H_2 \ldots H_{m-1} H_m H'_1 H'_2 \ldots H'_{m-1} H'_m$)

It should be appreciated that substring2(S) and substring2 (reverse(S)) may have duplicates.

Where the sequence S corresponds to an intron, the value V=signature (S) is a signature for that intron.

Where the sequence S corresponds to an exon, the value V=signature (S) is a signature for that exon.

Where the sequence S corresponds to a plurality of introns in a gene, the value V is an intron signature for that gene. For example, suppose a gene has the form:
<EXON$_1$><INTRON$_1$><EXON$_2$><INTRON$_2$>
<EXON$_3$><INTRON$_3$><EXON$_4$>

Then the introns for that gene are:
<INTRON$_1$><INTRON$_2$><INTRON$_3$>
and V=signature(<INTRON$_1$><INTRON$_2$><INTRON$_3$>) may be considered an intron signature of the gene.

As noted above, the value V1 may be considered the signature of a sequence and the additional processing described in steps 4 to 7 need not always be used.

The hashing application(s) 114 may be used to determine the hash functions. The permuting application(s) 116 may be used to determine the permuting functions.

If a gene codes for a protein P, then a mapping from the intron signature of the gene to the protein P may be stored.

EXAMPLES

Example 1

For illustration purposes the FNV1-64 Bit hash function (described above and shown in Appendix I) is used. For this and the next example the FNV_offset_basis was 14695981039346656037 and the FNV_prime was 1099511628211.

The example alphanumeric string: "123456" results in the following forward and reverse patterns (where the independent entities are separated here by a pipe character ("|") for readability). The third element "21" is underlined to aid in this description.

Forward pattern:
1|2|21|12|3|32|23|321|123|4|43|34|432|234|4321|1234|5|
54|45|543|345|5432|2345|54321|12345 ♀|65|56|654|
456|6543|3456|65432|23456|654321|123456
Reverse Pattern:
6|5|56|65|4|45|54|456|654|3|34|43|345|543|3456|6543|
2|23|32|234|432|2345|5432|23456|65432|1|12|21|123|
321|1234|4321|12345|54321|123456|654321

With reference to the description above, the alphanumeric string "123456" corresponds to the sequence $S = s_1 s_2 \ldots s_k$, and the elements or substrings shown between the pipe characters correspond, e.g., to S'=substrings2(S), where each element between the pipe characters is an element $S'_j$ in S'.

Each independent entity (i.e., each $S'_j$), separated here by a pipe character ("|") is hashed to produce a corresponding series of hash values (corresponding, e.g., to the values $H_1$, $H_2 \ldots H_{m-1}$, $H_m$ in the exemplary method described above). For the example here, the string of hash values (using the FNV1-64 Bit hash function) is (again with the elements conveniently separated by a pipe character, and again the third element is underlined to aid in this description).

```
12638153115695167470|12638153115695167469|590699460983228294
|590700560494856536|12638153115695167468|590698361471600182|
590699460983228292|15670681827632549363|15672520211074539707
|12638153115695167467|590697261959971938|590698361471600176|
15669688968632464052|15671527352074454392|13065275120612763629 |
14904296279238663669|12638153115695167466|590696162448343722 |
590697261959971940|15668726895957968621|15670675230562780069|
12436292896790463621|14248556340437519069|3217329580524563918|
12191037851845371770|12638153115695167465|590695062936715486|
590696162448343720|15667742833050908942|15669691167655720410|
11788148384315486969|13715240424343679337|12922639516191071529|
16952591664661362097|13438112598656879770|1222894297566385272
```

For example, the third element of the forward string is the substring "21", and the hash of "21" (using the FNV1-64 Bit hash function) is "590699460983228294".

A hash function is applied to the forward pattern (or hash string) above to produce a hash on the forward hash string, e.g., in this case: 3689337779037222387. This corresponds, e.g., to the value V1 in the description above, where the second function F is a hash function.

Note that in some cases the value of V1 is a function of the forward string S as well as of the hash of the entire forward string S (since the entire forward string is one of the substrings).

As noted above, in some embodiments this value V1 may be used as the signature of the string. Preferred embodiments, however, also use the reverse string (reverse(S)) to determine a signature.

The reverse string R=reverse(S) is "654321", and substrings2(R) produces the reverse substring list (here the 4th element "65" is underlined to aid in this description):
6|5|56|
65|4|45|54|456|654|3|34|43|345|543|3456|6543|2|23|
32|234|432|2345|5432|23456|65432|1|12|21|123|321|
1234|4321|12345|54321|123456|654321

This list corresponds to the $R_j$ elements in step 5 above, and a corresponding hash value is determined for each element (corresponding to $H'_j$ in step 5 above). This produces the reverse hash string (with elements again conveniently separated by a pipe character and again with the 4th element underlined to aid in the description):

```
12638153115695167465 | 12638153115695167466 | 590696162448343720 |
590695062936715486 | 12638153115695167467 | 590697261959971940 |
590696162448343722 | 15669691167655720410 | 15667742833050908942 |
12638153115695167468 | 590698361471600176 | 590697261959971938 |
15670675230562780069 | 15668726895957968621 | 13715240424343679337 |
11788148384315486969 | 12638153115695167469 | 590699460983228292 |
590698361471600182 | 15671527352074454392 | 15669688968632464052 |
14248556340437519069 | 12436292896790463621 | 16952591664661362097 |
12922639516191071529 | 12638153115695167470 | 590700560494856536 |
590699460983228294 | 15672520211074539707 | 15670681827632549363 |
14904296279238663669 | 13065275120612763629 | 12191037851845371770 |
3217329580524563918 | 1222894297566385272 | 13438112598656879770
```

For example, the 4th element of the reverse string is the substring "65", and the hash of "65" (using the FNV1-64 Bit hash function) is 590695062936715486.

A hash function is applied the reverse pattern (or string) above to produce a hash on the reverse hash string, e.g., in this case: 1117762966676293023. This corresponds, e.g., to the value V2 in the description above, where the second function F is a hash function.

Finally a signature is determined that is a function of the combined strings, corresponding, e.g., to the value V in step 7 above, and in this example:

V=Hash on Combined Hash String: 3332613321992290737

It should thus be appreciated that V=3332613321992290737 may be referred to as a signature of the string "123456".

End of Example 1

Example 2

In another example, the initial string is "ATCGTA", and the following tables summarize the results, again using the FNV1-64 Bit hash function:

| Forward string | |
|---|---|
| Hash Pattern | A\|T\|TA\|AT\|C\|CT\|TC\|CTA\|ATC\|G\|GC\|CG\|GCT\|TCG\|GCTA\|ATCG\|T\|TG\|GT\|TGC\|CGT\|TGCT\|TCGT\|TGCTA\|ATCGT\|A\|AT\|TA\|ATG\|GTA\|ATGC\|CGTA\|ATGCT\|TCGTA\|ATGCTA\|ATCGTA |
| Hash String | 12638153115695167390\|12638153115695167371\|590591708843663728\|590612599564599598\|12638153115695167388\|590610400541343296\|590591708843663730\|15594149221254432385\|15595930430091755881\|12638153115695167384\|590606002494830347\|590610400541343315\|15590207472068052965\|15577910534020601073\|16525184219191093854\|18090951936444459308\|12638153115695167371\|590591708843663734\|590606002494830364\|15577914932067113921\|15594170111975368854\|8535402655004371111\|8531571956492441047\|13618834825267319684\|13014269025115236752\|12638153115695167390\|590612599564599598\|590591708843663728\|15595930430091755885\|15590226163765732565\|18090995916909 72276\|693751697801798470\|13018231665022552392\|11118523393142201364\|7367017868097455385\|4751635947032993777 |
| Hash on Hash String | 15044728929743794989 |

| Reverse string | |
|---|---|
| Reverse Hash Pattern | A\|T\|TA\|AT\|G\|GT\|TG\|GTA\|ATG\|C\|CG\|GC\|CGT\|TGC\|CGTA\|ATGC\|T\|TC\|CT\|TCG\|GCT\|TCGT\|TGCT\|TCGTA\|ATGCT\|A\|AT\|TA\|ATC\|CTA\|ATCG\|GCTA\|ATCGT\|TGCTA\|ATCGTA\|ATGCTA |
| Reverse Hash String | 12638153115695167390\|12638153115695167371\|590591708843663728\|590612599564599598\|12638153115695167384\|590606002494830364\|590591708843663734\|15590226163765732565\|15595930430091755885\|12638153115695167388\|590610400541343315\|590606002494830347\|15594170111975368541\|15577914932067113921\|693751697801798470\|18090995916909 72276\|12638153115695167371\|590591708843663730\|590610400541343296\|15577910534020601073\|15590207472068052965\|8531571956492441047\|8535402655004371111\|11118523393142201364\|13018231665022552392\|12638153115695167390\|590612599564599598\|590591708843663728\|15595930430091755881\|15594149221254432385\|18090951936444459308\|16525184219191093854\|13014269025115236752\|13618834825267319684\|4751635947032993777\|7367017868097455385 |
| Hash on Reverse Hash String | 18106942616671776455 |
| Hash on Combined Hash String: | 3043950445422507503 |

End of Example 2

Example 3

Figure 6:
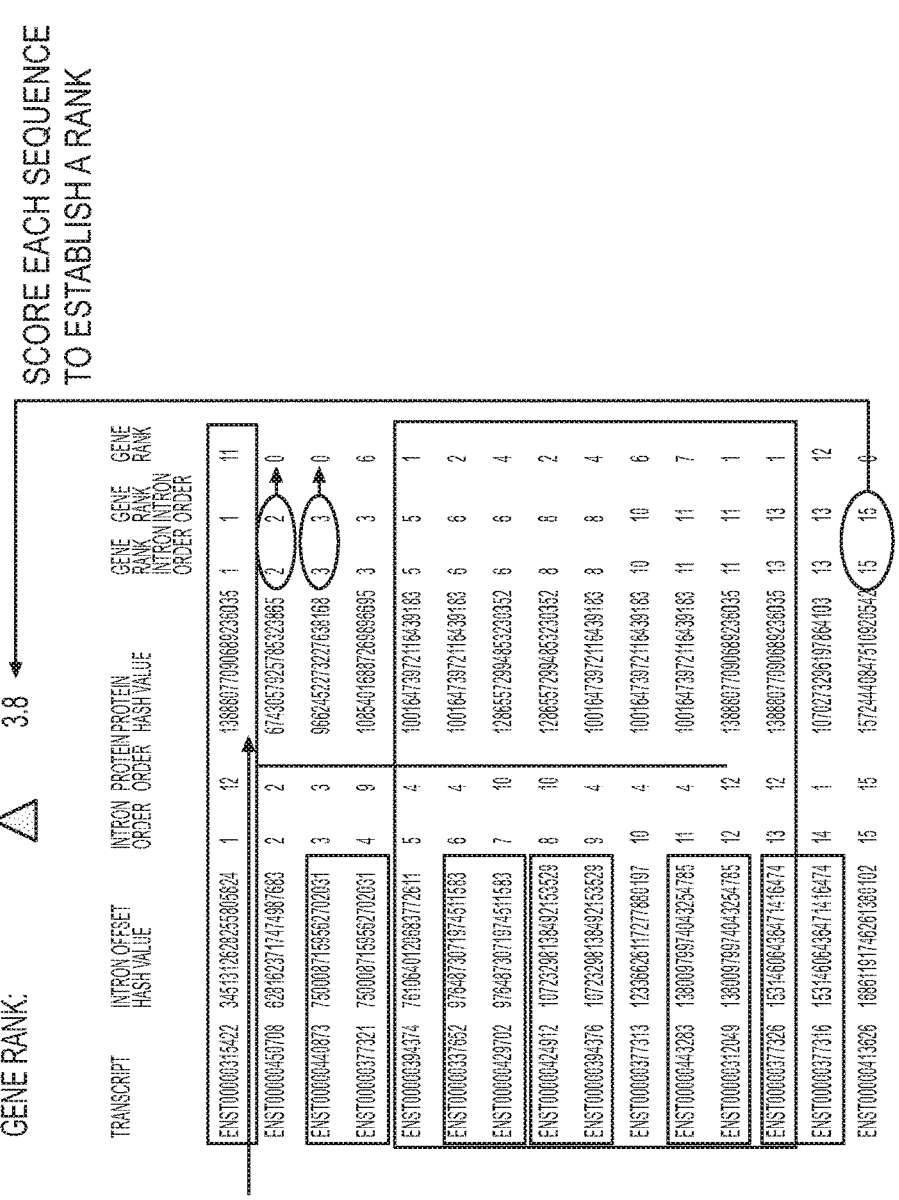
FIGS. 6-A to 6-F are screen shots of a web-based tool according to embodiments hereof.

FIGS. 6-G to 6-O are screen shots of additional aspects of a web-based tool according to exemplary embodiments hereof. As shown in the drawings, samples of consecutive intron offsets may be used to determine which signatures rank or correspond closest to protein. As shown herein, the system may be used to find sub-intron sequences that (preferably perfectly) order protein signatures for the transcript set. These are non-coding sub-sequences validated by ordering protein signatures, it is believed that they are likely to have some relative relationship to protein.

It is believed that most non-coding polypeptides are disassembled (some are not) and that the system disclosed herein may be used to:
- distinguish and precisely discover these non-coding polypeptides
- identify ranking methods and correlate tipping points that trigger disassembly
- formulaically associate identified sequences with protein characterizations
- identify sequences for individuals and evaluate impact to treatment regimes End of Example 3

Fractions

Recall that the string S resulted in a sequence of m values $H_1, H_2 \ldots H_{m-1}, H_m$, and that in step 3 above, the value V1 was determined as a function $F(H_1 H_2 \ldots H_{m-1} H_m)$. In the embodiments and examples above the hash values were taken on entire sequence of hash values associated with a string. However, it may be the case that fewer than all of the m values in the sequence should be considered. Accordingly, in some embodiments the function F may use a sliding window over fewer than all m values in the sequence. For the purposes of this discussion, assume that the window is of size k<m for some k. This will result in multiple signatures of fractions or portions of the sequence.

$$V_{11} = F(H_1 \ldots H_k)$$

$$V_{12} = F(H_2 \ldots H_{k+1})$$

$$V_{13} = F(H_3 \ldots H_{k+2})$$

$$\ldots$$

$$V_{1j} = F(H_{m-k} \ldots H_m)$$

Figure 5:
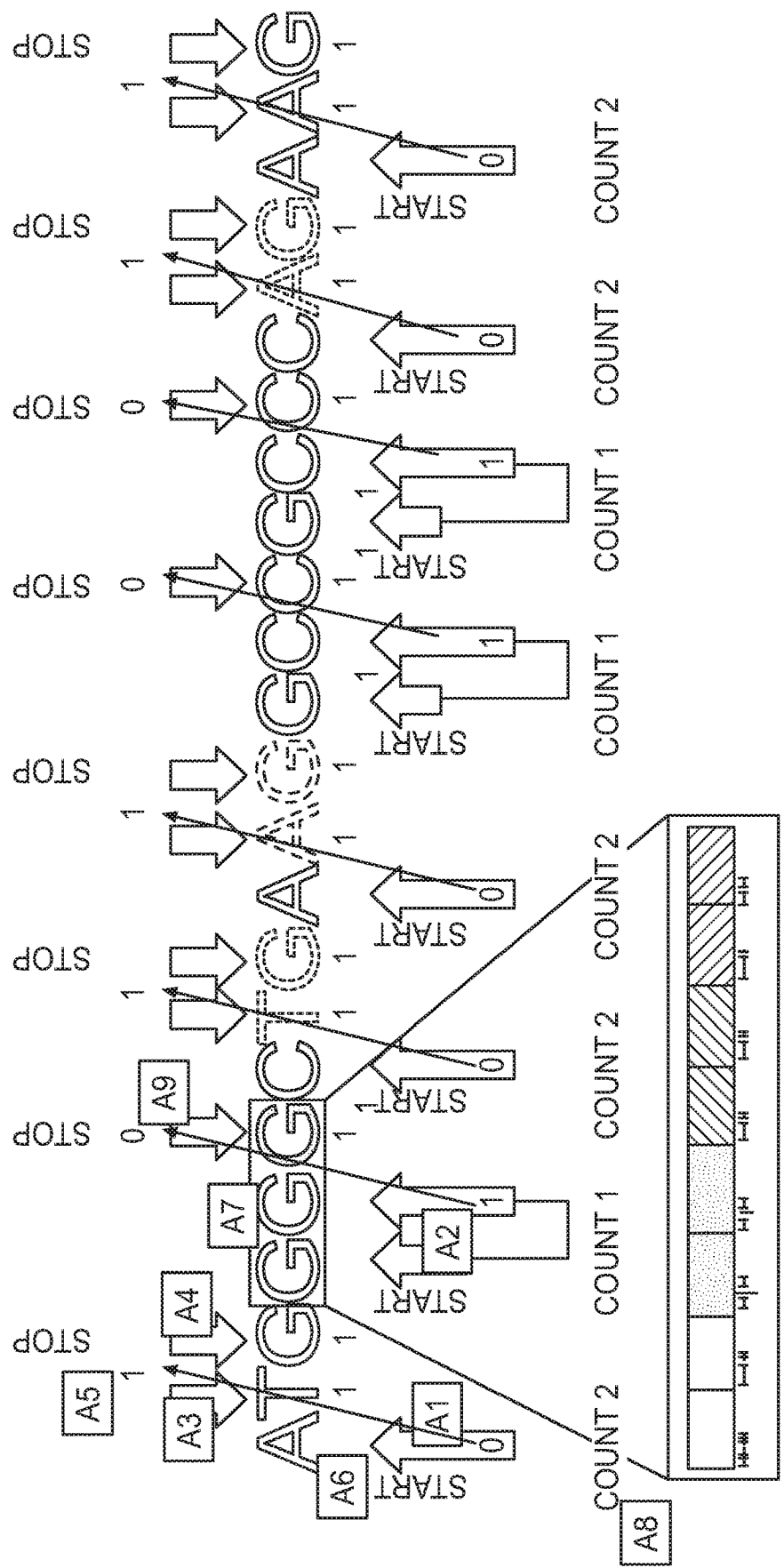
FIGS. 5-A to 5-B shows aspects of fractional analysis according to embodiments hereof.

For example, as shown in FIG. 5-A, a window of size 18 is used to determine the hash of fractions of the sequence of hashes (i.e., in this example k=18). As the window moves from right to left, it covers 18 different portions of the sequence of hashes (i.e., it covers 18 different hashes). These different portions or sequences may be referred to as fractions.

As an example, the window size may be set, arbitrarily, to be half the length of the sequence.

As shown in FIG. 5-B, a window, preferably of fixed size, is used to obtain multiple signatures for a particular sequence, one signature for each position of the window. For a sequence $P_1, P_2, P_3, \ldots P_k \ldots P_m$, where each Pi is a subsequence of an input string S (e.g., a generated by the pattern function described above), a window of size k determines signatures of $P_1$ to $P_k$, and of $P_2$ to $P_{k+1}$, and of $P_3$ to $P_{k+1}$, etc., up to $P_{m-k}$ to $P_m$. It should be apparent that if k=m (i.e., if the window is the size of the pattern sequence the single signature using all of the pattern elements will be obtained).

It should be appreciated that the fractions used to determine multiple signatures need not all use the same window sizes or start locations. For example, a window may be used to determine signatures that omit the end patterns.

Fractions may allow for looking at chunks or portions of a DNA sequence (e.g., an intron sequence) to look for improved protein ordering correlations and relationships as compared to other similar relationships obtained for other fractions of the DNA sequence. For example, a boundary recognized by a fraction that orders protein may be a marker for a splicing site, in which case the system will allow a user to rank and discover some or all viable splicing sites.

Preferably the function determines the hash of consecutive hashes and adjacent hashes, although this is not required.

Reporting Algorithm

This section describes an exemplary approach to generating a report for a specific offset, window size sequence direction (Forward/Reverse) of gene introns. Exemplary source code implementing this algorithm is shown in the source code appendix (Appendix I hereto) which is considered part of this application for all purposes.

In the following description the i-th transcript in a sequence is denoted Ti, the hash (H) of protein sequence for the i-th transcript is denoted $H(P)_{Ti}$, and the hash of the intron sequence for the i-th transcript is denoted $H(I)_{Ti}$.

The approach is described, without loss of generality, with reference to a particular example: Gene: MEN1, Offset: 23, Window size: 231880, Direction: Forward. The example MEN1 has 15 transcripts.

Precondition

1. All forward protein sequence of the gene transcripts have been patterned and hashed.

$H(P)_{Ti}$ Ti (for i from 1 to #transcripts)

2. Intron sequence for specific offset, window size and direction of gene transcripts have been patterned and hashed:

$H(I)_{Ti}$ Ti (for i from 1 to #transcripts)

Pair Rules

For the purposes of this algorithm there two categories of pairs, Type 1 pairs (for introns) and Type 2 pairs (for proteins).

1. Sort transcripts by $H(I)_{Ti}$, if two transcripts are next to each other and their protein hashes $H(P)_{Ti}$ are same, they will be count as a type 2 pair.

2. If a transcript has same sort position for sorted by protein hash $H(P)_{Ti}$ and by intron hash $H(I)_{Ti}$ it will be counted as a type 1 pair.

Step 1:

Sort transcripts by $H(P)_{Ti}$

Example: The sorted $H(P)_{Ti}$ transcripts for MEN1 (Offset: 23, Window size: 231880) are shown in the table below:

| Transcript | $H(P)_{Ti}$ | Pair Sort Position | Rank Position |
|---|---|---|---|
| ENST00000377316 | 1070273296197864103 | 1 | 1 |
| ENST00000450708 | 6743057925785323865 | 2 | 2 |
| ENST00000440873 | 9662452273227638168 | 3 | 3 |
| ENST00000394374 | 10016473972116439183 | 4 | 4 |
| ENST00000337652 | 10016473972116439183 | 4 | 4 |

| Transcript | H(P)$_{Ti}$ | Pair Sort Position | Rank Position |
|---|---|---|---|
| ENST00000377313 | 10016473972116439183 | 4 | 4 |
| ENST00000443283 | 10016473972116439183 | 4 | 4 |
| ENST00000394376 | 10016473972116439183 | 4 | 4 |
| ENST00000377321 | 10854016887269896695 | 5 | 9 |
| ENST00000429702 | 12865572994853230352 | 6 | 10 |
| ENST00000424912 | 12865572994853230352 | 6 | 10 |
| ENST00000312049 | 13888077090689236035 | 7 | 12 |
| ENST00000315422 | 13888077090689236035 | 7 | 12 |
| ENST00000377326 | 13888077090689236035 | 7 | 12 |
| ENST00000413626 | 15724440847510920542 | 8 | 15 |

Note: the difference between Pair Sort Position and Rank Position is how to handle the multiple transcripts in same position. For example if there is 5 transcripts in position 4, the next position for pair sort position is 5 and rank position is 9

Step 2:
Sort transcripts by H(I)$_{Ti}$.
Example: The sorted H(I)$_{Ti}$ transcripts for MEN1 (Offset: 23, Window size: 231880) are shown in the table below:

| Transcript | Intron Offset Hash Value | Gene Rank Intron Order | Protein Order (Rank position) |
|---|---|---|---|
| ENST00000377313 | 167613066517741313 | 1 | 4 |
| ENST00000394374 | 2503961881512634917 | 2 | 4 |
| ENST00000394376 | 5164633206682038560 | 3 | 4 |
| ENST00000424912 | 5164633206682038560 | 4 | 10 |
| ENST00000337652 | 5819545816596913902 | 6 | 4 |
| ENST00000429702 | 5819545816596913902 | 5 | 10 |
| ENST00000443283 | 7189214929071588867 | 7 | 4 |
| ENST00000440873 | 9351644970681852145 | 8 | 3 |
| ENST00000377321 | 9351644970681852145 | 9 | 9 |
| ENST00000377316 | 9534311961692397952 | 10 | 1 |
| ENST00000377326 | 9534311961692397952 | 11 | 12 |
| ENST00000315422 | 12292542568658633110 | 12 | 12 |
| ENST00000312049 | 15081914161581960811 | 13 | 12 |
| ENST00000450708 | 16379423582671150862 | 14 | 2 |
| ENST00000413626 | 18300401426631122607 | 15 | 15 |

Note: Protein order in this table is Rank Position of Step 1.

From this table, we can see some of transcripts automatically match the Pair Rule 1 (e.g., ENST00000377313 and ENST00000394374). However for some transcripts which have same Gene Rank Intron order may not ordered properly for Pair Rule 1.

Step 3: Reorder
Step 3.1 Regroup Transcripts by Gene Rank Intron Order
Example:

| Rank Position (Gene Rank Intron Order) | Transcript (protein order) |
|---|---|
| 1 (1) | ENST00000377313 (4) |
| 2 (2) | ENST00000394374 (4) |
| 3 (3) | ENST00000424912 (10) |
|  | ENST00000394376 (4) |
| 4 (5) | ENST00000429702 (10) |
|  | ENST00000337652 (4) |
| 5 (7) | ENST00000443283 (4) |
| 6 (8) | ENST00000440873 (3) |
|  | ENST00000377321 (9) |
| 7 (10) | ENST00000377316 (1) |
|  | ENST00000377326 (12) |
| 8 (12) | ENST00000315422 (12) |
| 9 (13) | ENST00000312049 (12) |
| 10 (14) | ENST00000450708 (2) |
| 11 (15) | ENST00000413626 (15) |

Step 3.2 Reorder in the Individual Group to Make Sure Having Max Match Paired Count.
In the example, after this step Group 3 will be fixed.

| Transcript | Intron Offset Hash Value | Gene Rank Intron Order | Protein Order (Rank position) |
|---|---|---|---|
| ENST00000377313 | 167613066517741313 | 1 | 4 |
| ENST00000394374 | 2503961881512634917 | 2 | 4 |
| ENST00000394376 | 5164633206682038560 | 3 | 4 |
| ENST00000424912 | 5164633206682038560 | 3 | 10 |
| ENST00000429702 | 5819545816596913902 | 5 | 10 |
| ENST00000337652 | 5819545816596913902 | 5 | 4 |
| ENST00000443283 | 7189214929071588867 | 7 | 4 |
| ENST00000440873 | 9351644970681852145 | 8 | 3 |
| ENST00000377321 | 9351644970681852145 | 8 | 9 |
| ENST00000377316 | 9534311961692397952 | 10 | 1 |
| ENST00000377326 | 9534311961692397952 | 10 | 12 |
| ENST00000315422 | 12292542568658633110 | 12 | 12 |
| ENST00000312049 | 15081914161581960811 | 13 | 12 |
| ENST00000450708 | 16379423582671150862 | 14 | 2 |
| ENST00000413626 | 18300401426631122607 | 15 | 15 |

Step 4: Protein Order Percentage
POP=Paired Transcripts Count/Total Transcripts Count.
For this example, see FIG. 6-E, Blue matches Pair Rule 1 and Yellow Matched Pair Rule 2. In this example POP=12/15*100%=80%

Step 5: Gene Rank (GR)

$$GR = \left( \sum_{1}^{Transcript\ Count} |Protein\ Order - Gene\ Rank\ Intron\ Order| \div Transcript\ Count \right)$$

In this example:

$GR = (|4 - 1| + |4 - 2| + |4 - 3| + |10 - 3| + |10 - 5| + |4 - 5| + |4 - 7| +$ $(|3 - 8| + |9 - 8| + |1 - 10| + |12 - 10| + |12 - 12| + |12 - 13| +$ $2 - 14| + |15 - 15|)/15$ $= (3 + 2 + 1 + 7 + 5 + 1 + 3 + 5 + 1 + 9 + 2 + 0 + 1 + 12 + 0)/15$ $= 52/15$ $= 3.47$

Step 6: Combined Rank (CR)
CR=GR−POP
In this example CR=3.47−0.8=2.67

Analyzing Data and Analysis Tools

A computer-implemented tool has been developed to use the above techniques, e.g., as an aid to analysis of genes. The tool supports analysis and query of results, exposing previously unknown information about relationships between strings and the underlying genes that they represent.

A current implementation uses a spreadsheet (e.g., Microsoft Corporation's Excel) to implement aspects of the database mechanism(s) 106, including aspects of the access mechanism(s) 108 and to support aspects of the user interface (UI) 126 and analysis 124. It should be appreciated that different and/or other implementations may be used for all or part of the system.

In a present implementation the system 100 generates some or all of the following information for a particular DNA (gene) sequence (assuming that the given gene sequence is known to code a particular protein): cDNA, intron, cds, cds+intron and protein for each transcript.

The system creates a signature value for these sequences using the signature algorithm(s) described above. Once the signatures are created they can stored and compared to other values.

In one exemplary implementation, to create a signature value for a sequences, the system performs the following for each input sequence string:
1. Generate pattern for the input sequence string.
2. Using hash (e.g., Rabin-Karp) method to hash each element of the sequence
3. Using hash (e.g., Rabin-Karp hash) for whole string generated by step 2.
4. For each sequence create three hash values:
    Forward hash value: input string is original string.
    Reverse hash value: input string reverse of original string.
    Combined hash value: concatenate forwarding string's step 2 output and reverse string's step 2 output and hash on the whole string.

FIGS. 6-A to 6-F are screen shots of a web-based tool according to embodiments hereof. As shown in FIG. 6-A, a user is presented with a menu screen allowing the user to select (in a known manner) a gene to be analyzed. FIG. 6-B shows the web-based user interface after the user selected the MEN1 genes on the menu in FIG. 6-A. As shown in FIG. 6-C, the user may then select the option "transcripts" to be presented with a number of transcripts of gene sequences in the MEN1 series. FIG. 6-D shows the screen presented to the user having selected transcript "ENST00000377316" from the list in FIG. 6-C. As shown in FIG. 6-C, the user is then able to see the signatures (denoted "Hash on Hash") for the DNA, cDNA, introns, CDS, CDS+Intron, and protein. In the example system shown, the user is provided with signatures using two hash functions (FNV and Rabin-Karp). Using the user interface, the user is also able to download files containing the strings that were hashed, in accordance, e.g., with the pattern and descriptions herein. By scrolling down the page (not shown) the user is also able to view the actual alphanumeric sequences for each of the DNA, cDNA, introns, CDS, CDS+Intron, and protein.

The MEN1 gene was obtained from http://asia.ensembl.org/*Homo_sapiens*/Gene/Summary?g=ENSG00000133895 and has the following properties:

| | |
|---|---|
| Name: | MEN1 |
| Location: | Chromosome 11: 64570988-64578766: −1 |
| Biotype: | protein_coding |
| Species: | *homo_sapiens* |
| Description: | multiple endocrine neoplasia I [Source: HGNC Symbol Acc: 7010] |
| Sequence Name: | chromosome:GRCh37:11:1:135006516:1 |
| Sequence Start: | 64570988 |
| Sequence End: | 64578766 |
| Sequence Strand: | −1 |
| Sequence Length: | 135006516 |

EXAMPLES

Example 4

Figure 4:
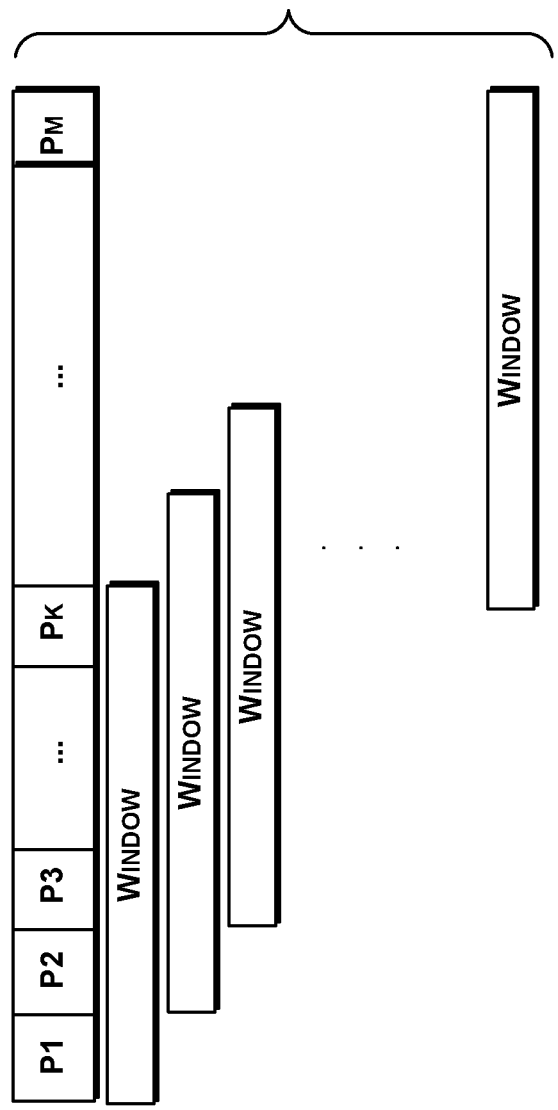
FIGS. 4-A and 4-B depict aspects of an exemplary use of the tools according to embodiments hereof.

With reference to FIGS. 4-A and 4-B, fourteen transcript strings (A10 in FIG. 4-A) were obtained from Ensembl a joint project between European Bioinformatics Institute (EBI) and the Wellcome Trust Sanger Institute (WTSI). Each string was processed using the software tool of the preferred embodiment to produce a summary hash as described. For each transcript string (A10) a hash summary result was obtained representing the strings of the combined non-coding (A15) or intron regions. Separately and similarly a hash summary was obtained for the protein (A12).

It was expected that coding regions or exons of the transcript string will have some relationship that can be described to the protein the coding sequence was responsible for coding. With respect to non-coding regions however, the analysis tool, shows previously unknown and/or unexpected results. For example, for a given transcript string that the non-coding regions or strings would have a calculable relationship that can be described to the protein string, because the non-coding sequences were spliced out of the protein coding processes. The preferred embodiment of the software tool orders the hash summaries (at A11) reported for each transcript's protein string and aggregates sets of identical transcript hash summaries for the protein (at A12). For these transcripts a total of ten proteins (labeled 1-3, 4-5 and 10-14 [at A13 and A14]) are found to aggregate together, as shown in FIG. 4-A and summarized in the following table.

| Transcript | Intron | | Protein |
|---|---|---|---|
| ENST00000377326 | 1310430311095040203 | 1 | 961582320622866331 |
| ENST00000315422 | 17088450819809387979 | 2 | 961582320622866331 |
| ENST00000312049 | 17187018405732497315 | 3 | 961582320622866331 |
| ENST00000429702 | 2063183349407904355 | 4 | 2263954643625590701 |
| ENST00000424912 | 4576144991289260531 | 5 | 2263954643625590701 |
| ENST00000440873 | 13201712806137462353 | 6 | 3477712031604516857 |
| ENST00000377321 | 8075656226753920645 | 7 | 4628150512757047415 |
| ENST00000450708 | 12454455881478123639 | 8 | 8956001353592653527 |
| ENST00000377316 | 8785326746195670043 | 9 | 11757523824566879541 |
| ENST00000394376 | 6708259094357667407 | 10 | 16855769192414700791 |
| ENST00000443283 | 10564216813085021255 | 11 | 16855769192414700791 |
| ENST00000394374 | 11333147157648448431 | 12 | 16855769192414700791 |
| ENST00000377313 | 14242566224793934807 | 13 | 16855769192414700791 |
| ENST00000337652 | 16399785077146281741 | 14 | 16855769192414700791 |
| ENST00000413626 | 887952281200868857 | 15 | 17298696577104854583 |

Table sorted on Protein

Sorting the list on the Intron or non-coding region [at A16 in FIG. 4-B] alters the ordering of the report [A11, A17]. Using the FNV1-64 Bit algorithm the summary hash results for non-coding or intron regions of each transcript [A18] is used to determine the new order. Eight identical proteins, 2-3 [A22], 4-5 [A19], 11-12 [A20] and 13-14 [A21] aggregate in groups (FIG. 4-A) retaining the same order when sorted by Protein (FIG. 4-B). Because the intron sort [A16] retains 8 out of 14 proteins in the same order as compared to 10 out of 14 from the protein sort [A11] (as shown in FIG. 4-B and summarized in the following table), the software tool of the preferred embodiment exposes a phenomenon in the relationships between the patterns as summarized for the different letter sequences of the derivatives of different transcript strings.

| Transcript | Intron | | Protein |
|---|---|---|---|
| ENST00000312049 | 17187018405732497315 | 3 | 961582320622866331 |
| ENST00000315422 | 17088450819809387979 | 2 | 961582320622866331 |
| ENST00000337652 | 16399785077146281741 | 14 | 16855769192414700791 |
| ENST00000377313 | 14242566224793934807 | 13 | 16855769192414700791 |
| ENST00000440873 | 13201712806137462353 | 6 | 3477712031604516857 |
| ENST00000450708 | 12454455881478123639 | 8 | 8956001353592653527 |
| ENST00000394374 | 11333147157648448431 | 12 | 16855769192414700791 |
| ENST00000443283 | 10564216813085021255 | 11 | 16855769192414700791 |
| ENST00000377316 | 8785326746195670043 | 9 | 11757523824566879541 |
| ENST00000377321 | 8075656226753920645 | 7 | 4628150512757047415 |
| ENST00000394376 | 6708259094357667407 | 10 | 16855769192414700791 |
| ENST00000424912 | 4576144991289260531 | 5 | 2263954643625590701 |
| ENST00000429702 | 2063183349407904355 | 4 | 2263954643625590701 |
| ENST00000377326 | 1310430311095040203 | 1 | 961582320622866331 |
| ENST00000413626 | 887952281200868857 | 15 | 17298696577104854583 |

Table Sorted on Intron

End of Example 4

Example 5

Twenty four transcript strings were obtained from Ensembl. Each string was processed using the software tool of the preferred embodiment to produce a summary hash as described. For each transcript string a hash summary result was obtained representing the strings of the combined non-coding or intron regions. Separately and similarly a hash summary was obtained for the proteins.

The following table shows the result of sorting on the protein signatures:

| Transcript | Intron Signature | | Protein Signature |
|---|---|---|---|
| ENST00000600022 | 336069337401981665 | 1 | 142119522134335871 |
| ENST00000596765 | 6792396245347082591 | 2 | 142119522134335871 |
| ENST00000600453 | 1333464500302449009 | 3 | 274912888327747645 |
| ENST00000377139 | 1401950702850314167 | 4 | 599822721118128169 |
| ENST00000309877 | 3500466469779260885 | 5 | 599822721118128169 |
| ENST00000597198 | 12664695880196353495 | 6 | 599822721118128169 |
| ENST00000596756 | 5753147864166720445 | 7 | 1790513508481396327 |
| ENST00000596788 | 16450205569587877267 | 8 | 2841845673249605807 |
| ENST00000593818 | 3667036665604008805 | 9 | 2854104808605521459 |
| ENST00000598108 | 10973488229403211067 | 10 | 3742347706388988009 |
| ENST00000593922 | 7664889625632691391 | 11 | 4161456730837722045 |
| ENST00000599144 | 10730458390030790945 | 12 | 4161456730837722045 |
| ENST00000598808 | 18226414717541850689 | 13 | 4161456730837722045 |
| ENST00000597636 | 15160735210389694755 | 14 | 4574430544478214501 |
| ENST00000599223 | 135004449481568781 | 15 | 4696664564400853515 |
| ENST00000377135 | 17357289184018730005 | 16 | 4696664564400853515 |
| ENST00000601291 | 15345119798735198385 | 17 | 5088758021177718819 |
| ENST00000601373 | 18388356984833608167 | 18 | 6314347853646019857 |
| ENST00000442265 | 9508049019065143111 | 19 | 8059716187484349851 |
| ENST00000600911 | 7799811173638205117 | 20 | 10273527430379935103 |
| ENST00000595034 | 18115509547352263109 | 21 | 11146466382498232009 |
| ENST00000601809 | 15399976974887301353 | 22 | 14941449829288148431 |
| ENST00000596822 | 10775356244809827141 | 23 | 16177802495955475919 |
| ENST00000593337 | 11674524626717572719 | 24 | 17347988539395493931 |

The following table shows the result of sorting the above table on intron signatures:

| Transcript | Intron Signature | | Protein Signature |
|---|---|---|---|
| ENST00000599223 | 135004449481568781 | 15 | 4696664564400853515 |
| ENST00000600022 | 336069337401981665 | 1 | 142119522134335871 |
| ENST00000600453 | 1333464500302449009 | 3 | 274912888327747645 |
| ENST00000377139 | 1401950702850314167 | 4 | 599822721118128169 |
| ENST00000309877 | 3500466469779260885 | 5 | 599822721118128169 |
| ENST00000593818 | 3667036665604008805 | 9 | 2854104808605521459 |
| ENST00000596756 | 5753147864166720445 | 7 | 1790513508481396327 |
| ENST00000596765 | 6792396245347082591 | 2 | 142119522134335871 |
| ENST00000593922 | 7664889625632691391 | 11 | 4161456730837722045 |
| ENST00000600911 | 7799811173638205117 | 20 | 10273527430379935103 |
| ENST00000442265 | 9508049019065143111 | 19 | 8059716187484349851 |
| ENST00000599144 | 10730458390030790945 | 12 | 4161456730837722045 |
| ENST00000596822 | 10775356244809827141 | 23 | 16177802495955475919 |
| ENST00000598108 | 10973488229403211067 | 10 | 3742347706388988009 |
| ENST00000593337 | 11674524626717572719 | 24 | 17347988539395493931 |
| ENST00000597198 | 12664695880196353495 | 6 | 599822721118128169 |
| ENST00000597636 | 15160735210389694755 | 14 | 4574430544478214501 |
| ENST00000601291 | 15345119798735198385 | 17 | 5088758021177718819 |
| ENST00000601809 | 15399976974887301353 | 22 | 14941449829288148431 |
| ENST00000596788 | 16450205569587877267 | 8 | 2841845673249605807 |
| ENST00000377135 | 17357289184018730005 | 16 | 4696664564400853515 |
| ENST00000595034 | 18115509547352263109 | 21 | 11146466382498232009 |
| ENST00000598808 | 18226414717541850689 | 13 | 4161456730837722045 |
| ENST00000601373 | 18388356984833608167 | 18 | 6314347853646019857 |

End of Example 5

SUMMARY

Aspects of some of the inventions disclosed herein are summarized here. It will be appreciated that features of the inventions are susceptible to being combined in any combination without departing from the scope of the inventions as defined by the accompany claims. It should also be appreciated that this summary is not intended to limit the scope of the claims, nor should this summary be construed as encompassing all inventions or embodiments thereof disclosed herein.

In some aspects, an invention disclosed herein is a computer-implemented method, implemented by hardware in combination with software, the method comprising: (A) obtaining a representation of a nucleic acid sequence, wherein the nucleic acid sequence encodes a particular gene and the particular gene encodes a particular protein, the nucleic acid sequence comprising at least one intron; (B) determining an intron signature value corresponding to the at least one intron, the intron signature value being based on a first computational function applied to one or more portions of the representation of the nucleic acid sequence corresponding to the at least one intron; (C) determining a protein signature value corresponding to the particular protein, the protein signature value being based on a second computational function applied to a representation of the particular protein; and (D) forming, in a database, an association between the intron signature value and the protein signature value. In some aspects acts (A) to (D) may be repeated for each of a plurality of nucleic acid sequences.

In some aspects the method may include (F) applying a sort to the multiple intron signature values in the database and ordering a plurality of nucleic acid sequences in the database based on the sort. The method may include (F) applying a sort to multiple fields in the database, the sort of the fields being keyed on intron signature values in the database, and ordering a plurality of nucleic acid sequences in the database based on the sort. In some aspects the method may include using an ordering determined by the sort to determine or confirm a role or function of a portion of a given nucleic acid sequence.

In some aspects the method may include (F) using multiple intron signature values in the database to determine or confirm a role or function of a portion of a given nucleic acid sequence. The using may include (F)(1) applying a sort to the multiple intron signature values in the database; and (F)(2) ordering a plurality of nucleic acid sequences in the database based on the sort.

In some aspects the using my include (F)(1) applying a sort to multiple records in the database, the sort of the records being keyed on intron signature values in the database; and (F)(2) ordering a plurality of nucleic acid sequences in the database based on the sort.

The first computational function may be a first hash function. The second computational function may be a second hash function. In some cases the first hash function may be the same as the second hash function. In some cases the first and/or second hash functions may be an FNV hash function or a Rabin-Karp hash function. In some cases the first and/or second hash functions may be both non-cryptographic hash functions.

The one or more portions of the representation of the nucleic acid sequence corresponding to the at least one intron may comprise a first character string, and the first computational function may be applied to the first character string.

In some cases, determining the intron signature value in (B) may include (B)(1) determining the intron signature value based on a plurality of hash values of a corresponding plurality of substrings of the first character string.

In some cases the representation of the particular protein may comprise a second character string, and the second computational function may be applied to the second character string, and the protein signature value may be determined in (C) based on a hash function applied to a second plurality of hash values of a corresponding plurality of substrings of the second character string.

The nucleic acid sequence may represent a DNA sequence and may comprise a character string comprising letters selected from the group {A, C, G, T}. The nucleic acid sequence may represent an RNA sequence and may comprise a character string comprising letters selected from the group {A, C, G, U}. The representation of the particular protein may comprise an amino acid sequence and may comprise a character string comprising letters selected from the group {A, D, E, G, F, L, S, Y, C, W, L, P, H, Q, R, I, M, T, N, K, S, R, V}.

In some aspects the database may contain a plurality of intron signature values and a corresponding plurality of protein signature values, each of the intron signature values having been determined for and based on a portion of a corresponding nucleic acid sequence, the corresponding nucleic acid sequence encoding a particular gene, and each of the protein signature values having been determined for a protein associated with the corresponding nucleic acid sequence.

In some aspects the process may include providing a user interface to the database. The user interface to the database may comprise a spreadsheet. The user interface to the database may comprise a web-based interface. The user interface to the database may provide support for one or more of: (a) listing a plurality of intron signature values and associated protein signature values in the database; (b) sorting fields in the database wherein the sort may be keyed on intron signature values in the database; and (c) sorting fields in the database wherein the sort may be keyed on protein signature values in the database. The database may also contain an association between the nucleic acid sequence and the first signature value.

The database may also contain an association between the nucleic acid sequence and the second signature value.

The nucleic acid sequence may be identified in the database by a unique sequence identifier associated with the nucleic acid sequence.

The interface may provide support for: (c) sorting fields in the database wherein the sort may be keyed on unique sequence identifiers in the database.

The one or more portions of the representation of the nucleic acid sequence corresponding to the at least one intron may comprise an intron sequence, and, in (B), the first function may be applied to less than the entire intron sequence.

The one or more portions of the representation of the nucleic acid sequence corresponding to the at least one intron may comprise an intron sequence, and multiple intron signature values may be determined for a corresponding multiple distinct portions of the intron sequence.

An association may be formed in the database between a plurality of the multiple intron signature values and the protein signature value.

The multiple intron signature values corresponding to the multiple distinct portions of the intron sequence may be used to recognize a boundary or a marker for a splicing site in the nucleic acid sequence.

In some aspects the process may include determining a numerically sequential order of the intron signature value associated with the nucleic acid sequence relative to other intron signature values associated with other nucleic acid sequences in the database.

In some aspects the process may include using the numerically sequential order of the intron signature value relative to the other intron signature values to determine or confirm at least one aspect of a genetic function of the nucleic acid sequence.

The database may be stored in a non-transitory computer-readable storage medium

The nucleic acid sequence obtained in (A) may correspond to a nucleic acid sequence in a mammal. The mammal may be a human.

In some other aspects, an invention disclosed herein comprises a computer-implemented method, implemented by hardware in combination with software, the method including: (A) determining a particular intron signature value corresponding to a particular at least one intron, the particular intron signature value being based on a first computational function applied to one or more portions of a representation of a particular nucleic acid sequence corresponding to the particular at least one intron; (B) determining a particular protein signature value corresponding to a particular protein, the protein signature value being based on a second computational hash function applied to a representation of the particular protein; (C) adding a record to a database, the record comprising a first field for the particular intron signature value and a second field for the particular protein signature value, wherein the database may comprise a plurality of records corresponding to a plurality of nucleic acid sequences, each of the records comprising an intron signature value and a corresponding protein signature value, each of the intron signature values having been determined for and based on the first computational function applied to a portion of a corresponding nucleic acid sequence, the corresponding nucleic acid sequence encoding a particular gene, and each of the protein signature values having been determined based on a second computational hash function applied to a representation of a protein associated with the corresponding nucleic acid sequence.

In some additional aspects, the process may include (D) using the plurality of intron signature values in the database to determine or confirm at least one aspect of a genetic function or role of the particular nucleic acid sequence.

In some additional aspects, the using in (D) may include (D)(1) applying a sorting function to the plurality of records in the database, the sorting function being keyed on intron signature values.

In some additional aspects, the process may include determining a numerically sequential order of the particular intron signature relative to other intron signature values in the database.

In some additional aspects, the process may include using the numerically sequential order of the particular intron signature to determine or confirm at least one aspect of a genetic function or role of the particular nucleic acid sequence.

The nucleic acid sequences may be DNA sequences or RNA sequences.

The first computational function may be a first hash function. The second computational function may be a second hash function. The first hash function may be the same as the second hash function. The first and/or second hash functions may be an FNV hash function or a Rabin-Karp hash function. The first and/or second hash functions may be both non-cryptographic hash functions.

The one or more portions of the representation of the nucleic acid sequence corresponding to the particular at least one intron may comprise a first character string, and the first computational function may be applied to the first character string.

In some additional aspects, the process may include determining the particular intron signature value in (A) by (A)(1) determining the particular intron signature value based on a plurality of hash values of a corresponding plurality of substrings of the first character string.

The representation of the particular protein may comprise a second character string, and wherein the second computational function may be applied to the second character string, and the particular protein signature value may be determined in (B) based on a hash function applied to a second plurality of hash values of a corresponding plurality of substrings of the second character string.

The nucleic acid sequence may represent a DNA sequence and may comprise a character string comprising letters selected from the group {A, C, G, T}. The nucleic acid sequence may represent an RNA sequence and may comprise a character string comprising letters selected from the group {A, C, G, U}. The representation of the particular protein may comprise an amino acid sequence and may comprise a character string comprising letters selected from the group {A, D, E, G, F, L, S, Y, C, W, L, P, H, Q, R, I, M, T, N, K, S, R, V}.

The database may contain a plurality of intron signature values and a corresponding plurality of protein signature values, each of the intron signature values having been determined for and based on a portion of a corresponding nucleic acid sequence, the corresponding nucleic acid sequence encoding a particular gene, and each of the protein signature values having been determined for a protein associated with the corresponding nucleic acid sequence.

In some additional aspects, the process may include providing a user interface to the database. The user interface to the database may comprise a spreadsheet. The user interface to the database may comprise a web-based interface. The interface may provide support for one or more of: (a) listing a plurality of intron signature values and associated protein signature values in the database; (b) sorting fields in the database wherein the sort may be keyed on intron signature values in the database; and (c) sorting fields in the database wherein the sort may be keyed on protein signature values in the database. The database may contain an association between the nucleic acid sequence and the first signature value.

The database may contain contains an association between the nucleic acid sequence and the second signature value.

The particular nucleic acid sequence may be identified in the database by a unique sequence identifier associated with the particular nucleic acid sequence.

The interface provides support for: (c) sorting fields in the database wherein the sort may be keyed on unique sequence identifiers in the database.

The one or more portions of the representation of the nucleic acid sequence corresponding to the particular at least one intron may comprise an intron sequence, and wherein, in (A), the first function may be applied to less than the entire intron sequence.

The one or more portions of the representation of the nucleic acid sequence corresponding to the particular at least one intron may comprise an intron sequence, and multiple intron signature values may be determined for a corresponding multiple distinct portions of the intron sequence.

An association may be formed in the database between a plurality of the multiple intron signature values and the protein signature value.

The multiple intron signature values corresponding to the multiple distinct portions of the intron sequence may be used to recognize a boundary or a marker for a splicing site in the nucleic acid sequence.

In some additional aspects, the process may include determining a numerically sequential order of the intron signature value associated with the nucleic acid sequence relative to other intron signature values associated with other nucleic acid sequences in the database.

In some additional aspects, the process may include using the numerically sequential order of the intron signature value relative to the other intron signature values to determine or confirm at least one aspect of a genetic function of the nucleic acid sequence.

The database may be stored in a non-transitory computer-readable storage medium

The nucleic acid sequence obtained in (A) may correspond to a nucleic acid sequence in a mammal. The mammal may be a human.

The nucleic acid sequence may be a biologically derived DNA sequence.

In some other aspects, an invention disclosed herein comprises a computer implemented method, implemented by hardware in combination with software, the method comprising: (A) obtaining a particular character string, the particular character string being representation of a first one or more portions of a particular nucleic acid sequence, wherein the particular nucleic acid sequence may comprise a second one or more portions that encode a particular protein, the first one or more portions of the particular nucleic acid sequence being distinct from the second one or more portions of the particular nucleic acid sequence; (B) determining a plurality of hash values of a corresponding plurality of substrings associated with the particular character string; (C) determining a signature value for the first one or more portions of the particular nucleic acid sequence based on the first plurality of hash values; (D) forming an association in a database between the signature value for the first one or more portions of the particular nucleic acid sequence and the particular protein; and (E) using the association formed in (D) and other associations in the database between other signature values of other character strings to determine or confirm at least one aspect of a genetic function of the particular nucleic acid sequence.

In some aspects, each of the other character strings may comprise a representation of a corresponding one or more portions of a corresponding nucleic acid sequence distinct from the particular nucleic acid sequence.

The plurality of hash values may be determined in (B) using a first hash function applied the corresponding plurality of substrings.

The determining in (C) may be based on a second hash function applied to the first plurality of hash values.

The first hash function may be the same as the second hash function.

The plurality of substrings may comprise a plurality of substrings of a reverse of the particular character string. The plurality of substrings may comprise: (i) at least one single character from the particular character string, and (ii) at least one sequence of 2 or more directly adjacent characters from the particular character string. The plurality of substrings may comprise: at least one sequence being a reverse of 2 or more directly adjacent character from the particular character string.

The particular character string may correspond to one or more introns in the particular nucleic acid sequence.

The particular nucleic acid may represent a DNA sequence or an RNA sequence. The first character string may represent a DNA sequence or an RNA sequence in a mammal. The first character string may represent a DNA sequence or an RNA sequence in a human.

In some additional aspects, the process may include (F) providing access to the database keyed on signature values.

In yet some other aspects, an invention disclosed herein comprises a computer-implemented method, implemented by hardware in combination with software, the method comprising: (A) obtaining a representation of a nucleic acid sequence, the nucleic acid sequence comprising multiple non-overlapping nucleic acid subsequences, each of the nucleic acid subsequences encoding an amino acid; and (B) determining a particular amino acid encoded by a particular nucleic acid subsequence of the multiple non-overlapping nucleic acid subsequences, wherein the particular nucleic acid subsequence may comprise a first nucleotide, a second nucleotide adjacent to the first nucleotide, and a third nucleotide adjacent to the second nucleotide, by considering a nucleotide pair consisting of: (i) the first nucleotide and the second nucleotide, or (ii) the second nucleotide and the third nucleotide.

In yet some other aspects, an invention disclosed herein comprises a computer-implemented method of encoding a nucleic acid sequence, the method implemented by hardware in combination with software, the method comprising: (A) obtaining a representation of the nucleic acid sequence, the nucleic acid sequence comprising multiple non-overlapping nucleic acid subsequences, each of the nucleic acid subsequences encoding an amino acid; (B) determining a plurality of subsequences of the nucleic acid sequence, wherein the plurality of subsequences may be determined by a binary counting of the nucleic acid sequence; and (C) determining a digital signature for the nucleic acid sequence based on a computational hash function applied to the plurality of subsequences of the nucleic acid sequence.

In yet some other aspects, an invention disclosed herein comprises computer program product having computer readable instructions stored on non-transitory computer readable media, the computer readable instructions including instructions for implementing a computer-implemented process, the process operable on a device comprising hardware including memory and at least one processor and running a service on the hardware, the process comprising: any of the processes described above and/or in the claims hereof, alone or in combination.

In yet some other aspects, an invention disclosed herein comprises device, having: (a) hardware including memory and at least one processor, and (b) one or more processes running on the hardware, wherein the one or more processes are configured to: perform any of the processes described above and/or in the claims hereof, alone or in combination.

In yet some other aspects, an invention disclosed herein comprises a system comprising a device as described herein.

As noted, this section summarizes only some aspects of some of the inventions disclosed herein, and it should not be construed as encompassing all inventions or embodiments thereof disclosed or contemplated herein. It should further be appreciated that the aspects summarized herein may be combined in multiple ways, and all such combinations are contemplated herein.

DISCUSSION

In a biological system nucleotide codons or peptide sequences of amino acids encode and assemble the reproduction of more complex protein structures required for the function of the system. We devised and disclosed an encoding and decoding tool to calculate, identify and extract information and relationship sensitivities from sequences that are not directly used in the coding.

Nucleotide sequences in genetic DNA are typically referred to by way of a triplet codon or ternary used for the transferal of information to encode protein. With four letters for DNA (A, T, C, G) and different numbers of "letters" in the derivative mRNA and protein "alphabets," scientists have researched different combinations of nucleotides corresponding to single amino acids. Nucleotide doublets were considered insufficient to specify every amino acid. Scientists theorized that nucleotide triplets encoded amino acids. It was confirmed experimentally that three nucleotides specify each amino acid. These nucleotide triplets are called codons.

Separately, massively distributed computing systems, used for storing and reproducing documents of any type, necessarily disassemble each documents' elements into instructional re-assembly data which is stored in sets that are sorted, catalogued and used by the system to reproduce any document on demand. The base encoding for storage and reproduction is binary. Often, binary system code may enable a feature where any and every same or similar sequence of letters in the system can be discovered.

Since the discovery of the codon, nucleotide sequences have been classified to attempt to determine relevant relationships between their codon encoding for amino acids and the proteins, for various protein enabled functions that the amino acid codons encode. Separately, tRNA codon molecules (which also originate in DNA) float into the cytoplasm where they attract a corresponding amino acid. Once this occurs the ribosome lines up the tRNA codon that matches the mRNA codon one after another to make the amino acid sequence or peptide. DNA regions interspersed with identified coding sequences were discovered to be spliced out in the process of encoding a protein. Subsequently named junk DNA, the non-coding sequences were deemed not important to the resulting protein. Recently this "junk DNA" view has been revised to classify non-coding regions as performing regulatory functions within the cell.

In view of the above our tool and method of coding and decoding has revealed and can reveal specific information about sequential nucleotide relationships that were previously unknown. The information is useful, e.g., for the discovery of non-coding nucleotide sequences that also relate to the final protein coded by amino acid codon's that originated from DNA nucleotide coding sequences. The coding regions are referred to as exons and non-coding regions introns.

The inventor has discovered that it is desirable to segment the nucleotides that comprise the codon such that in reading the codon's sequence in either direction, the first nucleotide informs about the second and the second informs about itself or itself and the third.

The inventor has also discovered that it is also desirable to extend reading beyond the codon to adjacent and/or surrounding nucleotides in the extended sequence such that each nucleotide and each nucleotide relationship, whether or not restricted to the codon, is considered and analyzed.

The inventor has further discovered that it is desirable to discover boundary conditions to segment the nucleotide sequences of non-coding regions into fractions as sections that can be identified to be more or less influential on the outcome of a protein that was coded; whether to other coding sequences in proximity or separated by significant distance within the gene or chromosome.

In some aspects embodiments of the disclosed systems, methods, and devices may provide one or more tools that may support or enable one or more of the following:

a method, based on a prescribed set of rules, to reduce any of more than two letters repeating in a sequence to a binary encoding.

a method of counting sequences of different alphanumeric letters in a string and arranging them into patterns based on their retained sequence orders in forward and reverse.

- a method of segmenting a string comprised of sequences of any of four different alphanumeric letters. Any of the four letters may be segmented into a ternary or lots of three, as represented in DNA nucleotides of genetic sequences known in the prior art as a codon.
- a method of preserving the order of letters of a string in forward and/or reverse directions to establish a pattern. In the pattern the first letter is considered independent and the second letter (in sequence) is considered independent. Then the pattern in order of the first and second letters is considered in forward and reverse directions. Then the third letter is added and considered independent before a new pattern of third and second in order is considered. This is repeated for the sequence of second and third to complete the bi-directional pattern. Then the first letter is added to the pattern of second and third, bi-directionally and considered. The pattern continues until the end of the sequence string.
- a method to establish a signature using any known signature or hash method of any and every pattern for any part of and/or for the entire string.
- a method to compare patterns or using pattern signatures, to other patterns or pattern signatures including by ordering the patterns numerically or by ordinal structure or by a measurement of their relative positions.
- a method of highlighting certain pattern anomalies or characteristics specifically as related to the order of patterns for different strings of letter sequences when compared.

Those of ordinary skill in the art will realize and appreciate, upon reading this description, that the above list is merely exemplary of the applications supported by the processes, devices, and systems according to embodiments hereof.

It should be appreciated and understood that the DNA sequences used herein may be derived from human tissue. The human tissue can be diseased or normal.

Counting

During transcription or when editing and splicing exon from intron or during Ribosome reading mRNA codon matching tRNA to code amino acid peptides for protein, various forms of sequential counting may be taking place. It has conventionally been presumed that mRNA is read as a ternary (codon) and matched to tRNA. However, the inventor proposes that what is perceived to be a ternary (codon), may in fact be binary as proposed if the reader protein reads in either direction as follows:

if T or A, acknowledge two;
or if C or G, then if C or G acknowledge one or if T or A acknowledge two;

The process corresponds, at least in part, to skip-read-read or skip-skip-read depending on whether G and C or A and T is first and second encountered. Without significant change this is a more efficient reader and interpreter of the coded RNA code or the DNA code depending where the reading is occurring in the cell.

With reference to FIG. 5-C, for any alphanumeric sequence string arranged into ternary or codon units [A7], a binary arrangement is discovered to agree with known experimental output results from the corresponding ternary system. Such a method is described. The same rules for counting forward or backward along the string apply in reverse. For illustration only, counting is in a forward sequential direction beginning with the letter A followed by T followed by G until the end sequence of string [A6] where A is followed by A is followed by G.

Whereas in the ternary system comprised of letters A, T, G and C each letter representing a nucleotide of a single DNA strand or string; each set of three sequential letters are known to code a known amino acid nucleotide combination. An alternative binary encoding system to that which is conventionally known, and that produces the identical result, is introduced here. Rules for the binary encoding group A with T and G with C. When A or T of a ternary is first [A1] encountered the next two letters [A3 and A4] are considered relative to the first one [A1]. Where C or G [A7] is first encountered, the next letter is considered, if it is a C or G [A2 of A7], the next letter is considered [A9 of A7] relative to the first two. In this manner consideration of letter sequences is relative and dependent on a binary encoding, where for any ternary, only the last two or last letters of the ternary determine the codon's classification for amino acid encoding.

In the conventional ternary system for classification as in this binary system, counting always begins with a starting nucleotide or letter [A1] and continues in units of three (3) the ending nucleotide or letter [A4] of the codon. For the classification of known amino acids using the DNA ternary system for each codon, the preferred binary system described herein is known to produce the identical result. Logic of the preferred embodiment is therefore determined based on meeting the same output of a proven alternative encoding.

It should be appreciated that this method modifies the present understanding because the read after a mutation would also be out-of-order for the codon depending on the nature of the mutation at the specific nucleotide.

Applying the logic of the preferred embodiment, a nucleotide string represented by ternary letters A and/or T and/or C and/or G can be classified in grouping of 1[A1] and 2 [A3 and A4] or 2 [A2] and 1 [A9] letters. Using information of the preferred embodiment a new method is derived to rank strings of sequences of letters or nucleotides. The method separates letters and letter sequences into independent entity units and preserves the bi-directional order of the independent entity cumulatively until the end of the string. For any given alphanumeric string similar to that represented here:
1|2|21|12|3|32|23|321|123|4|43|34|432|234|4321|1234|
5|54|45|543|345|5432|2345|54321|12345|6|65|56|654|
456|6543|3456|65432|23456|654321|23456
the first character is segmented from the string to form an independent entity; the second character is segmented from the string to form an independent entity; the first and second character are segmented from the string to form an independent entity; the second character and first character are segmented from the string to form an independent entity; the third character is segmented from the string to form an independent entity; the third and the second character are segmented from the string to form an independent entity; the second and third characters are segmented from the string to form an independent entity; the third character, the second character and the first character are segmented from the string to form an independent entity. The pattern continues until the end of the given string, as illustrated above.

Therefore the preferred embodiment establishes a new ordinal pattern from a given sequence, which retains the sequential order of the original in forward and reverse directions, iteratively and cumulatively until the end of the string. The preferred embodiment may produce the same pattern starting from either end of the string or it may segment a string into two or more fractions and perform the same on each of the fractions. Following the completion of segmentation for the string, the string and each and every independent entity produced is summarized using a hash or similar function that reduces each independent entity and the string to a representation that is consistent for all independent entities patterned from the string. A hash of all the independent entity hashes derived from the pattern in forward or reverse directions is produced to summarize the information. Finally a hash of the hash of the hashes for each independent entity in the forward direction and in the reverse direction is obtained as a summary of the entire string.

Computing

Programs that implement such methods (as well as other types of data) may be stored and transmitted using a variety of media (e.g., computer readable media) in a number of manners. Hard-wired circuitry or custom hardware may be used in place of, or in combination with, some or all of the software instructions that can implement the processes of various embodiments. Thus, various combinations of hardware and software may be used instead of software only.

Figure 7:
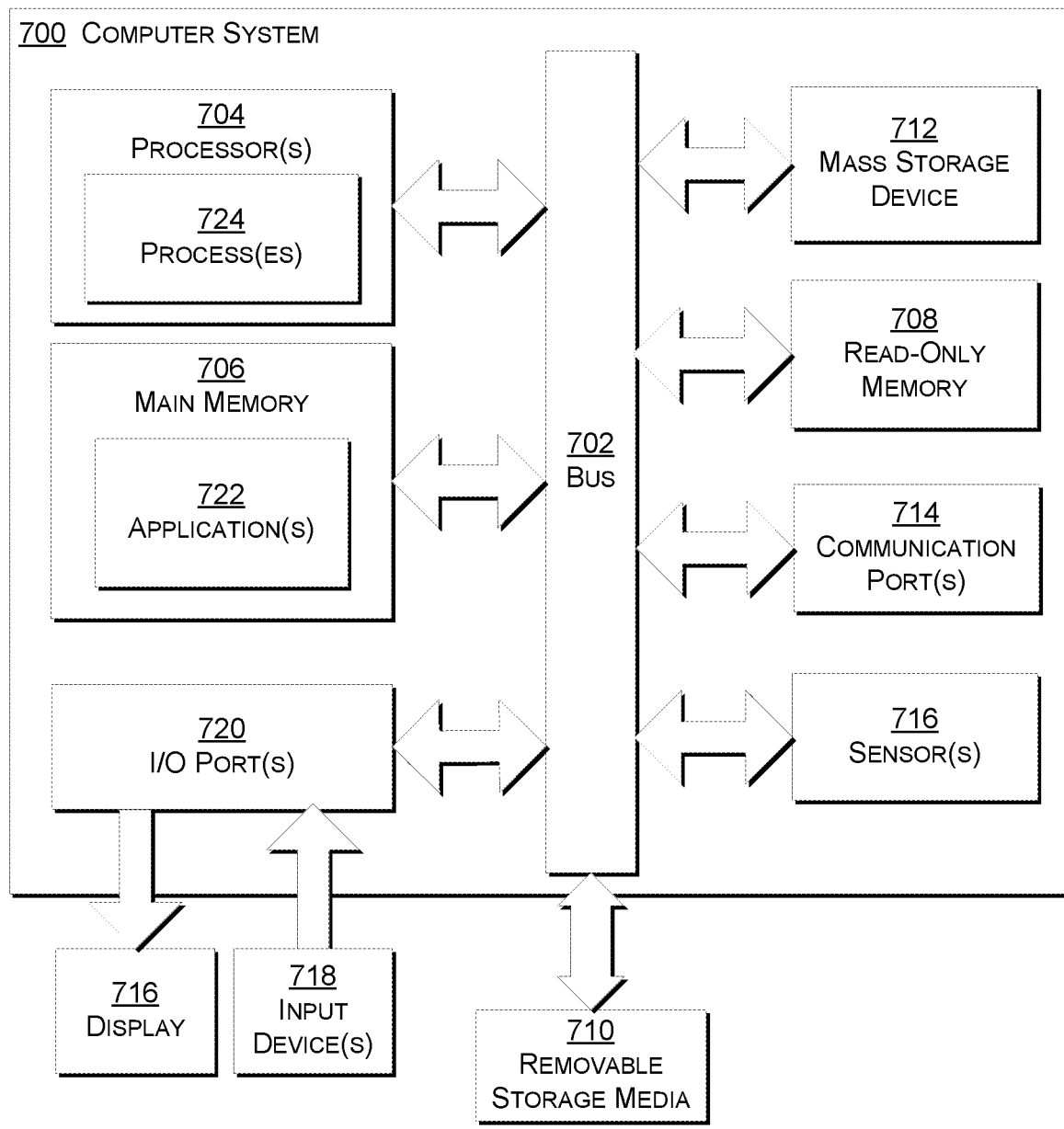
FIG. 7 is a schematic diagram of a computer system used in embodiments hereof.

FIG. 7 is a schematic diagram of a computer system 700 upon which embodiments of the present disclosure may be implemented and carried out.

According to the present example, the computer system 700 includes a bus 702 (i.e., interconnect), one or more processors 704, one or more communications ports 714, a main memory 706, removable storage media 710, read-only memory 708, and a mass storage 712. Communication port(s) 714 may be connected to one or more networks by way of which the computer system 700 may receive and/or transmit data.

As used herein, a "processor" means one or more microprocessors, central processing units (CPUs), computing devices, microcontrollers, digital signal processors, or like devices or any combination thereof, regardless of their architecture. An apparatus that performs a process can include, e.g., a processor and those devices such as input devices and output devices that are appropriate to perform the process.

Processor(s) 704 can be (or include) any known processor, such as, but not limited to, an Intel® Itanium® or Itanium 2® processor(s), AMD® Opteron® or Athlon MP® processor(s), or Motorola® lines of processors, and the like. Communications port(s) 714 can be any of an RS-232 port for use with a modem based dial-up connection, a 10/100 Ethernet port, a Gigabit port using copper or fiber, or a USB port, and the like. Communications port(s) 714 may be chosen depending on a network such as a Local Area Network (LAN), a Wide Area Network (WAN), a CDN, or any network to which the computer system 700 connects. The computer system 700 may be in communication with peripheral devices (e.g., display screen 716, input device(s) 718) via Input/Output (I/O) port 720. Some or all of the peripheral devices may be integrated into the computer system 700, and the input device(s) 718 may be integrated into the display screen 716 (e.g., in the case of a touch screen).

Main memory 706 can be Random Access Memory (RAM), or any other dynamic storage device(s) commonly known in the art. Read-only memory 708 can be any static storage device(s) such as Programmable Read-Only Memory (PROM) chips for storing static information such as instructions for processor(s) 704. Mass storage 712 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices may be used.

Bus 702 communicatively couples processor(s) 704 with the other memory, storage and communications blocks. Bus 702 can be a PCI/PCI-X, SCSI, a Universal Serial Bus (USB) based system bus (or other) depending on the storage devices used, and the like. Removable storage media 710 can be any kind of external hard-drives, floppy drives, IOMEGA® Zip Drives, Compact Disc-Read Only Memory (CD-ROM), Compact Disc-Re-Writable (CD-RW), Digital Versatile Disk-Read Only Memory (DVD-ROM), etc.

Embodiments herein may be provided as one or more computer program products, which may include a machine-readable medium having stored thereon instructions, which may be used to program a computer (or other electronic devices) to perform a process. As used herein, the term "machine-readable medium" refers to any medium, a plurality of the same, or a combination of different media, which participate in providing data (e.g., instructions, data structures) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory, which typically constitutes the main memory of the computer. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications.

The machine-readable medium may include, but is not limited to, floppy diskettes, optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols; and/or (iv) encrypted in any of a variety of ways well known in the art.

A computer-readable medium can store (in any appropriate format) those program elements that are appropriate to perform the methods.

As shown, main memory 706 is encoded with application(s) 722 that support(s) the functionality as discussed herein (an application 722 may be an application that provides some or all of the functionality of one or more of the mechanisms described herein). Application(s) 722 (and/or other resources as described herein) can be embodied as software code such as data and/or logic instructions (e.g., code stored in the memory or on another computer readable medium such as a disk) that supports processing functionality according to different embodiments described herein.

During operation of one embodiment, processor(s) 704 accesses main memory 706 via the use of bus 702 in order to launch, run, execute, interpret or otherwise perform the logic instructions of the application(s) 722. Execution of application(s) 722 produces processing functionality of the service(s) or mechanism(s) related to the application(s). In other words, the process(es) 724 represents one or more portions of the application(s) 722 performing within or upon the processor(s) 704 in the computer system 700.

It should be noted that, in addition to the process(es) 724 that carries(carry) out operations as discussed herein, other embodiments herein include the application 722 itself (i.e., the un-executed or non-performing logic instructions and/or data). The application 722 may be stored on a computer readable medium (e.g., a repository) such as a disk or in an optical medium. According to other embodiments, the application 722 can also be stored in a memory type system such as in firmware, read only memory (ROM), or, as in this example, as executable code within the main memory 706 (e.g., within Random Access Memory or RAM). For example, application 722 may also be stored in removable storage media 710, read-only memory 708, and/or mass storage device 712.

The application(s) 722 may correspond, at least in part, to one or more of the mechanisms 102 shown in FIG. 1. For example, the hashing mechanism(s) 114 may conveniently be implemented by one or more application(s) 722 that, when executed, run as corresponding processes 724.

Those skilled in the art will understand that the computer system 700 can include other processes and/or software and hardware components, such as an operating system that controls allocation and use of hardware resources.

Those skilled in the art will understand that the computer system 700 can include other processes and/or software and hardware components, such as an operating system that controls allocation and use of hardware resources.

As discussed herein, embodiments of the present invention include various steps or operations. A variety of these steps may be performed by hardware components or may be embodied in machine-executable instructions, which may be used to cause a general-purpose or special-purpose processor programmed with the instructions to perform the operations. Alternatively, the steps may be performed by a combination of hardware, software, and/or firmware. The term "module" refers to a self-contained functional component, which can include hardware, software, firmware or any combination thereof.

One of ordinary skill in the art will readily appreciate and understand, upon reading this description, that embodiments of an apparatus may include a computer/computing device operable to perform some (but not necessarily all) of the described process.

Embodiments of a computer-readable medium storing a program or data structure include a computer-readable medium storing a program that, when executed, can cause a processor to perform some (but not necessarily all) of the described process.

Where a process is described herein, those of skill in the art will appreciate that the process may operate without any user intervention. In another embodiment, the process includes some human intervention (e.g., a step is performed by or with the assistance of a human).

As used in this description, the term "portion" means some or all. So, for example, "A portion of X" may include some of "X" or all of "X". In the context of a sequence, the term "portion" means some or all of the sequence.

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

In general, as used herein, including in the claims, unless the word "only" is specifically used in a phrase, it should not be read into that phrase.

As used herein, including in the claims, the phrase "overlap" means "at least partially overlap." Unless specifically stated, "overlap" does not mean fully overlap. Thus, by way of non-limiting example, the sequence "ABCD" may be said to overlap the sequence "BCDE" and the sequence "ABCDE" and the sequence "DEFG".

As used herein, including in the claims, the phrase "distinct" means "at least partially distinct." Unless specifically stated, distinct does not mean fully distinct. Thus, e.g., the phrase, "X is distinct from Y" means that "Xis at least partially distinct from Y," and does not mean that "X is fully distinct from Y." Thus, as used herein, including in the claims, the phrase "X is distinct from Y" means that X differs from Y in at least some way. It should be appreciated that two fully or partially overlapping sequences can be distinct. As a non-limiting example, the sequence "BCD" overlaps and is distinct from the sequence "ABCDE".

As used herein, including in the claims, a list may include only one item, and, unless otherwise stated, a list of multiple items need not be ordered in any particular manner. A list may include duplicate items. For example, as used herein, the phrase "a list of XYZs" may include one or more "XYZs".

It should be appreciated that the words "first", "second", "third," and so on, if used in the claims, are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

No ordering is implied by any of the labeled boxes in any of the flow diagrams unless specifically shown and stated. When disconnected boxes are shown in a diagram the activities associated with those boxes may be performed in any order, including fully or partially in parallel.

While the invention has been described in connection with and with respect to protein, DNA, and RNA molecules, those of ordinary skill in the art will realize and appreciate, upon reading this description, that these techniques may be applied to other molecules, including molecules in a genome (including non-coding molecules).

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

We claim:

1. A computer-implemented method, implemented by hardware in combination with software, said method comprising:
   (A) obtaining a representation of a nucleic acid sequence, wherein said nucleic acid sequence represents at least a portion of a particular transcript of a particular human gene, said particular human gene having multiple transcripts, and
   wherein said particular transcript of said particular human gene corresponds to a particular protein, and
   wherein said particular transcript of said particular human gene comprises multiple introns, and
   wherein said nucleic acid sequence corresponds to a plurality of said multiple introns;
   (B) determining, using a patterning mechanism, a plurality of subsequences of said representation of said nucleic acid sequence, wherein said nucleic acid sequence has a length n, and wherein said patterning mechanism produces $O(n^2)$ subsequences;
   (C) determining a plurality of subsequence portion signature values by:
      (C)(1) determining, for each particular subsequence of said plurality of subsequences, a particular subsequence portion signature value, said particular subsequence portion signature value being based on a first computational function applied to said particular subsequence of said representation of said nucleic acid sequence; and then
      (C)(2) determining an intron portion signature value from said subsequence portion signature values, said intron portion signature value being determined based on a second computational function applied to said plurality of subsequence portion signature values, said intron portion signature value comprising a unique sequence identifier for said nucleic acid sequence;
   (D) determining a protein signature value corresponding to said particular protein;
   (E) forming, in a database, an association between said intron portion signature value and said protein signature value;
   (F) repeating acts (A) to (E) for at least one other transcript of said particular human gene, said at least one other transcript being distinct from said particular transcript; and then
   (G) determining an order of a given intron portion signature value associated with a given nucleic acid sequence relative to intron portion signature values associated with nucleic acid sequences of multiple distinct transcripts of the particular human gene, said order being based on said unique sequence identifiers associated with intron portion signature values in the database;
   (H) applying a sort to fields in the database, said sort keyed on unique sequence identifiers associated with intron portion signature values in the database; and then
   (I) using said order to evaluate and/or determine a role and/or function of said particular transcript and/or said given nucleic acid sequence and a given protein.

2. The method of claim 1, further comprising:
   ordering intron portion signature values and protein signature values in said database based on said sort.

3. The method of claim 1, wherein said using in (I) uses multiple intron portion signature values in said database to determine and/or confirm said role and/or function of a portion of said given nucleic acid sequence.

4. The method of claim 3, wherein applying said sort in (H) comprises:
   (H)(1) applying a sort to said multiple intron portion signature values in said database; and
   (H)(2) ordering a plurality of nucleic acid sequences in said database based on said sort.

5. The method of claim 1, wherein applying said sort in (H) comprises:
   (H)(1) applying a sort to multiple records in said database, said sort of said records being keyed on intron portion signature values in said database; and
   (H)(2) ordering a plurality of nucleic acid sequences in said database based on said sort.

6. The method of claim 5, wherein, in (H)(2), said plurality of nucleic acid sequences and associated protein signatures are ordered based on said sort.

7. The method of claim 1, wherein the nucleic acid sequence comprises: (i) a DNA sequence, and the representation comprises a character string comprising letters selected from {A, C, G, T}; or (ii) an RNA sequence, and the representation comprises a character string comprising letters selected from {A, C, G, U}.

8. The method of claim 1, wherein said one said nucleic acid sequence comprise an intron sequence, and wherein multiple intron portion signature values are determined for a corresponding multiple distinct portions of said intron sequence.

9. The method of claim 8, wherein an association is formed in said database between a plurality of said multiple intron portion signature values and said protein signature value or nucleic acid sequence considered to represent said particular protein.

10. The method of claim 1, wherein said given nucleic acid sequence is a biologically derived DNA sequence.

11. The method of claim 1, wherein said first computational function comprises a first computational hash function.

12. The method of claim 1, wherein said protein signature value is based on a second computational function applied to a representation of said particular protein.

13. The method of claim 12, wherein said a second computational function comprises a second computational hash function.

14. The method of claim 1, wherein said nucleic acid sequence corresponds to all of said multiple introns.

15. The method of claim 1, wherein said using in (I) identifies one or more sequences for a treatment regime and/or selects among gene transcripts.

16. The method of claim 1, wherein said using in (I) uses said order to evaluate and/or determine said role and/or function of said portion of said particular human gene.

17. The method of claim 1, wherein the protein signature value is based on a nucleic acid sequence considered to represent said particular protein.

18. The method of claim 1, wherein two identical nucleic acid sequences will have the same intron portion signature values and the same unique sequence identifiers.

19. The method of claim 1, wherein said order is based on ordinal values of said unique sequence identifiers associated with intron portion signature values in the database.

20. An article of manufacture comprising non-transitory computer-readable media having computer-readable instructions stored thereon, the computer-readable instructions including instructions for implementing a computer-implemented method, said method operable on a device comprising hardware including memory and at least one processor and running a service on said hardware, said method comprising the method of claim 1.

21. A system comprising:
(a) hardware including memory and at least one processor, and
(b) a service running on said hardware, wherein said service is configured to:
perform the method of claim 1.

22. The method of claim 1, wherein said patterning mechanism produces k subsequences, where k is a function of $n^2$.

23. The method of claim 1, wherein said patterning mechanism produces $O(n^2)$ subsequences in a forward direction and $O(n^2)$ subsequences in a reverse direction.

24. A computer-implemented method, implemented by hardware in combination with software, said method comprising:
(A) for each particular nucleic acid sequence of a plurality of nucleic acid sequences, wherein said plurality of nucleic acid sequences correspond to a plurality of transcripts of a particular human gene, said particular human gene having multiple transcripts, and
wherein said particular nucleic acid sequence represents at least part of a particular transcript of said particular human gene, and wherein said particular transcript of said particular human gene comprises multiple introns, and wherein said particular nucleic acid sequence has a length n,
and wherein at least one transcript of said particular human gene corresponds to a particular protein, and wherein at least some of said particular nucleic acid corresponds to a plurality of said multiple introns:

(A)(0) determining a plurality k of subsequences of a representation of said nucleic acid sequence, wherein the number of subsequences k is a function of $n^2$;
(A)(1) determining a plurality of subsequence portion signature values corresponding to said plurality of subsequences, wherein, for a given subsequence of said plurality of subsequences, the corresponding subsequence portion signature value is based on a first computational function applied to a representation of said given subsequence;
(A)(2) determining an intron portion signature value from said subsequence portion signature values, said intron portion signature value being determined based on a computational function applied to said plurality of subsequence portion signature values, said intron portion signature value comprising a unique sequence identifier for said nucleic acid sequence;
(A)(3) determining a particular protein signature value corresponding to said particular protein;
(A)(4) forming, in a database, an association between one or more of said intron portion signature values and said particular protein signature value, wherein each of said intron portion signature values is associated with a corresponding unique sequence identifier in the database; and then
(B) applying a sort to fields in said database, said sort being keyed on unique sequence identifiers associated with intron portion signature values in the database, and then
(C) determining an order for a plurality of nucleic acid sequences in said database based on said sort; and then
(D) using said order to evaluate and/or determine a role and/or function of a portion of at least one transcript of said particular human gene and a given protein.

25. The method of claim 24, wherein said particular protein signature value is based on a second computational function applied to a representation of said particular protein.

26. The method of claim 24, wherein said representation of said particular nucleic acid sequence comprises a character string comprising letters selected from {A, C, G, T}; or (ii) a character string comprising letters selected from {A, C, G, U}.

27. A computer-implemented method, implemented by hardware in combination with software, said method comprising:
(a) determining an order of a given intron portion signature value associated with a given nucleic acid sequence from a given transcript of a particular human gene relative to intron portion signature values associated with nucleic acid sequences of multiple other transcripts of said particular human gene, wherein said given transcript of said particular human gene comprises multiple introns, and wherein said given nucleic acid sequence corresponds to a plurality of said multiple introns, said order being based on unique sequence identifiers associated with intron portion signature values in a database;
(b) applying a sort to fields in the database, said sort keyed on unique sequence identifiers associated with intron portion signature values in the database; and
(c) using said order to evaluate and/or determine a role and/or function of at least one transcript of said particular human gene or said given nucleic acid sequence and a given protein, wherein said database comprises multiple associations, each association being between one or more intron portion signature values and corresponding protein signature values, wherein a particular protein signature value corresponds to a particular protein, each of said intron portion signature values corresponding to multiple introns of a corresponding transcript of said particular human gene, each of said intron portion signature values being based on a first computational function applied to a plurality k of subsequence portion signature values corresponding to intron portions of a particular nucleic acid sequence corresponding to said multiple introns, wherein, for a particular nucleic acid sequence of length n, the number k of subsequence portion signature values is $O(n^2)$, and wherein, in said database, each of said intron portion signature values is associated with a corresponding unique sequence identifier, and wherein said particular nucleic acid sequence represents at least a portion of a particular human gene, and wherein at least one transcript of said particular human gene corresponds to a particular protein, and wherein said particular nucleic acid sequence corresponds to at least a portion of at least one intron of said particular human gene.

28. The method of claim 27, wherein the given nucleic acid sequence is a biologically derived DNA sequence.

\* \* \* \* \*

SEQUENCE LISTING

<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atggggctga aggccgccca gaag                                          24